(12) United States Patent
Chien et al.

(10) Patent No.: US 7,785,782 B2
(45) Date of Patent: Aug. 31, 2010

(54) DEVICE AND METHOD FOR IN-LINE BLOOD TESTING USING BIOCHIPS

(75) Inventors: David Y. Chien, Alamo, CA (US); Bruce H. Phelps, Clayton, CA (US); Yiu-Lan Fong, Lafayette, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 1021 days.

(21) Appl. No.: 10/733,767

(22) Filed: Dec. 12, 2003

(65) Prior Publication Data

US 2005/0048519 A1    Mar. 3, 2005

Related U.S. Application Data

(60) Provisional application No. 60/432,665, filed on Dec. 12, 2002, provisional application No. 60/435,287, filed on Dec. 23, 2002.

(51) Int. Cl.
 *C12Q 1/68* (2006.01)
(52) U.S. Cl. .................................. 435/6; 6/287.2
(58) Field of Classification Search ......... 436/514–518; 435/6, 4, 7.1, 7.2, 7.91–7.95, 287.1–287.3, 435/287.7–287.9, 288.4–289.1; 422/57, 422/58
See application file for complete search history.

(56) References Cited

U.S. PATENT DOCUMENTS

| | | | |
|---|---|---|---|
| 2,896,619 A | 7/1959 | Bellamy, Jr. | |
| 4,708,850 A | 11/1987 | Husain | |
| 4,987,071 A | 1/1991 | Cech et al. | |
| 5,024,238 A | 6/1991 | Guirguis | |
| 5,037,746 A | 8/1991 | Cech et al. | |
| 5,116,742 A | 5/1992 | Cech et al. | |
| 5,144,019 A | 9/1992 | Rossi et al. | |
| 5,180,818 A | 1/1993 | Cech et al. | |
| 5,225,337 A | 7/1993 | Robertson et al. | |
| 5,254,678 A | 10/1993 | Haseloff et al. | |
| 5,298,612 A | 3/1994 | Jennings et al. | |
| 5,354,855 A | 10/1994 | Cech et al. | |
| 5,383,885 A | 1/1995 | Bland | |
| 5,415,282 A | 5/1995 | Kienholz | |
| 5,472,840 A | 12/1995 | Stefano | |
| 5,494,814 A | 2/1996 | Haseloff et al. | |
| 5,496,698 A | 3/1996 | Draper et al. | |
| 5,543,508 A | 8/1996 | Haseloff et al. | |
| 5,574,143 A | 11/1996 | Haseloff et al. | |
| 5,589,332 A | 12/1996 | Shih et al. | |
| 5,589,580 A | 12/1996 | Haseloff et al. | |
| 5,616,459 A | 4/1997 | Kramer et al. | |
| 5,626,843 A | 5/1997 | Skurkovich et al. | |
| 5,652,094 A | 7/1997 | Usman et al. | |
| 5,652,143 A | 7/1997 | Gombrich et al. | |
| 5,663,064 A | 9/1997 | Burke et al. | |
| 5,679,520 A | 10/1997 | Hogan et al. | |
| 5,698,687 A | 12/1997 | Eckstein et al. | |
| 5,707,835 A | 1/1998 | Haseloff et al. | |
| 5,712,128 A | 1/1998 | Been et al. | |
| 5,741,679 A | 4/1998 | George et al. | |
| 5,741,706 A | 4/1998 | Leavitt et al. | |
| 5,747,335 A | 5/1998 | Haseloff et al. | |
| 5,763,181 A | 6/1998 | Han et al. | |
| 5,766,942 A | 6/1998 | Haseloff et al. | |
| 5,769,811 A | 6/1998 | Stacey et al. | |
| 5,795,729 A | 8/1998 | Lee | |
| 5,840,874 A | 11/1998 | Haseloff et al. | |
| 5,843,658 A | 12/1998 | Uchiyama et al. | |
| 5,861,242 A * | 1/1999 | Chee et al. | 435/5 |
| 5,939,538 A | 8/1999 | Leavitt et al. | |
| 5,942,395 A | 8/1999 | Fournier et al. | |
| 5,972,595 A | 10/1999 | Kasila et al. | |
| 5,998,193 A | 12/1999 | Keese et al. | |
| 6,004,806 A | 12/1999 | McCall et al. | |
| 6,020,209 A * | 2/2000 | Narang et al. | 436/514 |
| 6,025,167 A | 2/2000 | Cech et al. | |
| 6,074,827 A * | 6/2000 | Nelson et al. | 435/6 |
| 6,087,484 A | 7/2000 | Goodchild | |
| 6,100,087 A | 8/2000 | Rossi et al. | |
| 6,127,114 A | 10/2000 | Haseloff et al. | |
| 6,127,173 A | 10/2000 | Eckstein et al. | |
| 6,140,491 A | 10/2000 | Usman et al. | |
| 6,162,396 A | 12/2000 | Bitensky et al. | |
| 6,168,948 B1 * | 1/2001 | Anderson et al. | 435/287.2 |
| 6,180,399 B1 | 1/2001 | Cech et al. | |
| 6,194,180 B1 | 2/2001 | Joyce | |

(Continued)

FOREIGN PATENT DOCUMENTS

GB    2 339 903    2/2000

(Continued)

OTHER PUBLICATIONS

U.S. Appl. No. 60/480,431, filed Jun. 20, 2003, Shyamala.

(Continued)

*Primary Examiner*—Ann Y Lam
(74) *Attorney, Agent, or Firm*—Mark Seka; Sunit Talapatra

(57) ABSTRACT

A device for in-line blood screening and testing using biochips is disclosed. The screening methods include nucleic acid amplification techniques and antibody/antigen assays to detect target molecules and agents indicative of infectious diseases or metabolic diseases.

54 Claims, 22 Drawing Sheets

U.S. PATENT DOCUMENTS

| | | | |
|---|---|---|---|
| 6,221,661 | B1 | 4/2001 | Hampel et al. |
| 6,251,599 | B1 | 6/2001 | Chen et al. |
| 6,251,666 | B1 | 6/2001 | Beigelman |
| 6,280,936 | B1 | 8/2001 | Burgin et al. |
| 6,287,768 | B1 | 9/2001 | Chenchik et al. |
| 6,287,821 | B1 | 9/2001 | Shi et al. |
| 6,323,186 | B1 | 11/2001 | Klaubert et al. |
| 6,329,209 | B1 | 12/2001 | Wagner et al. |
| 6,379,931 | B1 | 4/2002 | Rossi et al. |
| 6,387,617 | B1 | 5/2002 | Asher et al. |
| 6,399,392 | B1 | 6/2002 | Haugland et al. |
| 6,426,184 | B1 | 7/2002 | Gao et al. |
| 6,482,932 | B1 | 11/2002 | Beigelman et al. |
| 6,924,107 | B2 * | 8/2005 | Liu .............................. 435/6 |
| 2001/0053535 | A1 * | 12/2001 | Bashir et al. .................. 435/34 |
| 2002/0072084 | A1 | 6/2002 | Meserol |
| 2003/0134416 | A1 * | 7/2003 | Yamanishi et al. .......... 435/372 |
| 2004/0209353 | A1 | 10/2004 | Chien et al. |
| 2005/0048519 | A1 | 3/2005 | Chien et al. |

FOREIGN PATENT DOCUMENTS

| | | |
|---|---|---|
| WO | WO 98/15356 A | 4/1998 |
| WO | WO 99/26724 | 6/1999 |
| WO | WO 99/56630 | 11/1999 |
| WO | WO 02/30562 A | 4/2002 |

OTHER PUBLICATIONS

Cairns et al., "Catalytic DNA: A Novel Tool for Gene Suppression," *Curr. Drug Targets*, 2002, pp. 269-279, vol. 3, Bentham Science Publishers Ltd.

Carmi et al., "Cleaving DNA with DNA," *Proc. Natl. Acad. Sci.*, Mar. 1998, pp. 2233-2237, vol. 95.

Carson et al., "Simultaneous quantitation of 15 cytokines using a multiplexed flow cytometric assay," *Journal of Immunological Methods*, 1999, pp. 41-52, vol. 227, Nos. 1-2, Elsevier.

Davies et al., "Profiling of Amyloid β Peptide Variants Using SELDI ProteinChip® Arrays," *Biotechniques*, Dec. 1999, pp. 1258-1261, vol. 27, No. 6.

Fortina et al., "DOP-PCR Amplification of Whole Genomic DNA and Microchip-Based Capillary Electrophoresis," *Methods in Molecular Biology*, vol. 163: *Capillary Electrophoresis of Nucleic Acids*, vol. 2: *Practical Applications of Capillary Electrophoresis*, 2001, pp. 211-219, Humana Press Inc., Totowa, NJ.

Fortina et al., "Simple two-color array-based approach for mutation detection," *European J. Human Genetics*, Nov. 2000, pp. 884-894, vol. 8, No. 11.

Gildersleeve et al., "Development of a Genetic Selection for Catalytic Antibodies," *Bioorganic & Medicinal Chemistry Letters*, 2002, pp. 1691-1694, vol. 12, Elsevier Science Ltd.

Gilles et al., "Single nucleotide polymorphic discrimination by an electronic dot blot assay on semiconductor microchips," *Nature Biotechnology*, Apr. 1999, pp. 365-370, vol. 17, No. 4.

Hunt et al., "Detection of West Nile Virus Antigen in Mosquitoes and Avian Tissues by a Monoclonal Antibody-Based Capture Enzyme Immunoassay," *J. Clin. Microbiology*, Jun. 2002, pp. 2023-2030, vol. 40, No. 6.

Kong et al., "A Circular RNA-DNA Enzyme Obtained by in Vitro Selection," *Biochem. Biophys. Res. Commun.*, 2002, pp. 1111-1115, vol. 292, Elsevier Science (USA).

Lanciotti et al., "Nucleic Acid Sequence-Based Amplification Assays for Rapid Detection of West Nile and St. Louis Encephalitis Viruses," *Journal of Clinical Microbiology*, Dec. 2001, pp. 4506-4513, vol. 39, No. 12.

Nam et al., "Nanoparticle-Based Bio-Bar Codes for the Ultrasensitive Detection of Proteins," *Science*, Sep. 26, 2003, pp. 1885-1886, vol. 301.

Okamoto et al., "Microarray fabrication with covalent attachment of DNA using Bubble Jet technology," *Nature Biotechnology*, Apr. 2000, pp. 436-443, vol. 18, No. 4.

Petrik, "Microarray technology: the future of blood testing?" *Vox Sanguinis*, Jan. 2001, pp. 1-11, vol. 80, No. 1, Blackwell Science.

Rider et al., "A B Cell-Based Sensor for Rapid Identification of Pathogens," *Science*, Jul. 11, 2003, pp. 213-215, vol. 301.

Sambrook et al. (Eds.), *Molecular Cloning, A Laboratory Manual*, 2nd Edition, Chapter 14, Description of PCT Protocols, Cold Spring Harbor Laboratory Press, 1989.

Vaish et al., "Monitoring post-translational modification of proteins with allosteric ribozymes," *Nature Biotechnology*, Aug. 2002, pp. 810-815, vol. 20.

Wang et al., "A General Strategy for Effector-mediated Control of RNA-cleaving Ribozymes and DNA Enzymes," *J. Mol. Biol.*, 2002, pp. 33-43, vol. 318, Elsevier Science Ltd.

Wang et al., "A general approach for the use of oligonudeotide effectors to regulate the catalysis of RNA-cleaving ribozymes and DNAzymes," *Nuc. Acid Res.*, 2002, pp. 1735-1742, vol. 30, No. 8, Oxford University Press.

Yuen et al., "Microchip Module for Blood Sample Preparation and Nucleic Acid Amplification Reactions," *Genome Research*, Mar. 2001, pp. 405-412, vol. 11, No. 3, Cold Spring Harbor Laboratory Press.

\* cited by examiner

DEVICE AND METHOD FOR IN-LINE BLOOD TESTING USING BIOCHIPS

BACKGROUND OF THE INVENTION

This invention relates to the field of blood screening and provides improvements that enable more comprehensive, accurate and convenient screening to be performed, for detecting the presence of targeted molecules that indicate the presence of a pathogen, infectious agent or metabolic disease. More specifically, the invention provides a method and system for in-line blood screening, wherein an in-line removable screening capture device with biochips is provided between a blood collection needle and a blood collection bag, such that collected blood flows through the screening capture device and contacts the biochips before being collected in the blood collection bag. Alternatively, the biochips are provided in an inlet of the blood collection bag, inside the blood collection bag or inside a separate diversion blood collection bag.

Currently, blood banks use several individual assays to test for the presence of multiple agents or molecules associated with or indicative of a disease or condition. Exemplary agents or molecules include anti-HIV I/II antibodies, anti-HCV antibodies, HBV surface antigen, anti-HBC antibodies, liver enzyme (ALT), syphilis and HIV P24 antigen. Additionally, infectious agents such as pathogenic bacteria and fungi, prions and protozoa, including the causative agents of small pox, malaria, West Nile disease, Chagas disease, and variant Creutzfel Jacob disease (CJD) may be detected. Also, non-infectious agents such as molecules that indicate metabolic disorders, including the molecules measured in various metabolite panels, may be detected, including a lipid panel (cholesterol, triglycerides, LDLs and HDLs), thyroid hormone panel (T3, T4, TBP and TSH) and liver enzyme panel (ALT (alanine aminotransferase), ALP (alkaline phosphatase), AST (aspartate aminotransferase), GGT (gamma-glutamyl transferase), LDH (lactic acid dehydrogenase), bilirubin, and albumin).

The current methods involve collecting blood directly into a blood collection bag via a collection needle and collecting duct, with a very minute fraction of the collected blood being segregated into another compartment for testing/screening purposes. Current methods of blood screening, therefore, involve testing a very small portion, or sample, of the collected blood and may not effectively detect analytes that are sparsely dispersed in the blood. Some potential problems of testing small samples include (1) non-homogeneous distribution of the testing agent (or analyte), (2) micro-aggregation of the analytes and/or binding of the analytes to serum proteins, and (3) cross-contamination between samples taken for the various tests that may be conducted, such as in the nucleic acid technology assays (NAT).

Furthermore, performing multiple individual assays requires duplicative time and effort because the sample must be prepared and labeled for each individual assay. Additionally, the performance of multiple individual assays compounds the problem of appropriately labeling and tracking blood samples so that they can be correlated to the correct patient or donor. Errors and inaccuracies therefore can result from clerical errors in labeling, correlating and storing information generated from the multiple individual assays. Another problem is that too much blood may be used for testing because a separate sample is required for each of the various tests to be conducted.

Additionally, separating a collected blood sample into portions for multiple individual assays increases the potential for contamination, due to the additional handling required. Of course, the conduct of multiple individual assays also increases the risk that at least one assay will corrupted by contamination.

BRIEF SUMMARY OF THE INVENTION

The present invention provides a new platform technology for screening blood. The technology ensures that a much larger fraction of blood collected, even every drop, is tested. Under previous screening methods, only very small fractions of roughly 450 ml of collected blood was used for screening. For example, 0.5 ml was used for NAT testing, 20 µl each for anti-HIV I/II, anti-HCV, anti-HBC, ALT, and syphilis testing, and 100 µl each for HbsAg and HIV p24 testing. Using such small fractions creates a sampling risk, because the fractions may not be representative of the entire volume of collected blood. That is, disease agents that are relatively scarcely scattered in the collected blood may not be contained within a small fraction or volume. The present invention addresses this problem by ensuring a more thorough and more comprehensive screening of collected blood. The present invention also enables testing for hundreds of agents or molecules to be performed at once, rather than testing for a small number of agents or molecules in separate assays.

Accordingly, in one aspect, the invention provides for the use of an in-line screening capture device that includes one or more biochips. Advantageously, low density biochips can be used. The capture device is removable and can be arranged or located between a collection needle and collection bag, such that all collected blood flows through the screening capture device and thereby contacts the biochips. Alternatively, the screening capture device may be positioned at an inlet of a blood collection bag or even inside of a blood collection bag. The biochips bind target agents or molecules in the blood being tested and can then be used to detect the bound target agents and molecules. Preferably, the detection of target agents or molecules is facilitated by a separate multiplex assay system, or biochip processor, designed to execute target and/or signal amplification and antibody/antigen binding reactions. As an example, microfluidic technologies and chemiluminescent detection systems can be employed for detecting targeted agents or molecules on the biochips.

The invention also contemplates an in-line rapid assay system that enables blood testing to be completed simultaneously with or soon after the completion of blood collection.

The invention further includes a screening capture device for in-line screening of blood collected using a collection needle connected by a collection duct to a collection bag, comprising an inlet for blood collected from the collection needle; a biochip unit that captures target agents or molecules from the blood; and an outlet that drains the blood from the screening capture device to the collection duct. A method for using the screening capture device also is included. In alternative embodiments of the invention, the screening capture device and/or biochip are positioned at an inlet of a blood collection bag or inside of a blood collection bag.

The present invention provides at least the following advantages over currently known procedures for screening blood:

(1) The screening process uses an in-line capture technique; therefore, almost no collected blood is lost because practically every drop that goes to the collection bag flows through, or alternatively a large sample of the blood contacts, the screening capture device and/or biochips provided by the invention.

(2) The invention enables use of a multiplex assay system; all assays can be run on one or more of the biochips that contact the blood.

(3) The invention can employ low-density biochips, so adding additional targets, such as components of new emerging diseases, is easier and more efficient.

(4) The assays of the invention are rapid, due to minimized reaction times resulting from the use of micro-volumes of sample in a biochip processor.

(5) The "laboratory on a chip" screening system of the invention provides a confined environment for running the multiple assays. The screening capture unit and biochip processing unit are both self-sealed, consume little space and diminish the opportunity for human error and/or contamination that may be caused by exposing the sample to the surrounding environment or by extra handling of the sample required to conduct multiple individual assays.

(6) The detection systems employ technology that not only can detect the presence of a sequence indicative of a disease, but can also detect different genotypes of each agent as well as point mutations of the captured targets.

(7) The invention can employ assays that provide a quantitative readout, such as by controlling PCR cycle number. For instance, Taqman PCR technology works on such a principle. By using a standard, or calibrator, (i.e., with a known copy number) and comparing the cycle numbers of a test sample with the standard, it is possible to obtain a quantitative result.

BRIEF DESCRIPTION OF THE DRAWINGS

The accompanying drawings, which are incorporated in and constitute a part of the specification, illustrate presently preferred embodiments of the invention. Together with the general description given above and the detailed description given below, the drawings serve to explain principles of the invention.

DETAILED DESCRIPTION OF THE INVENTION

Figure 1A:
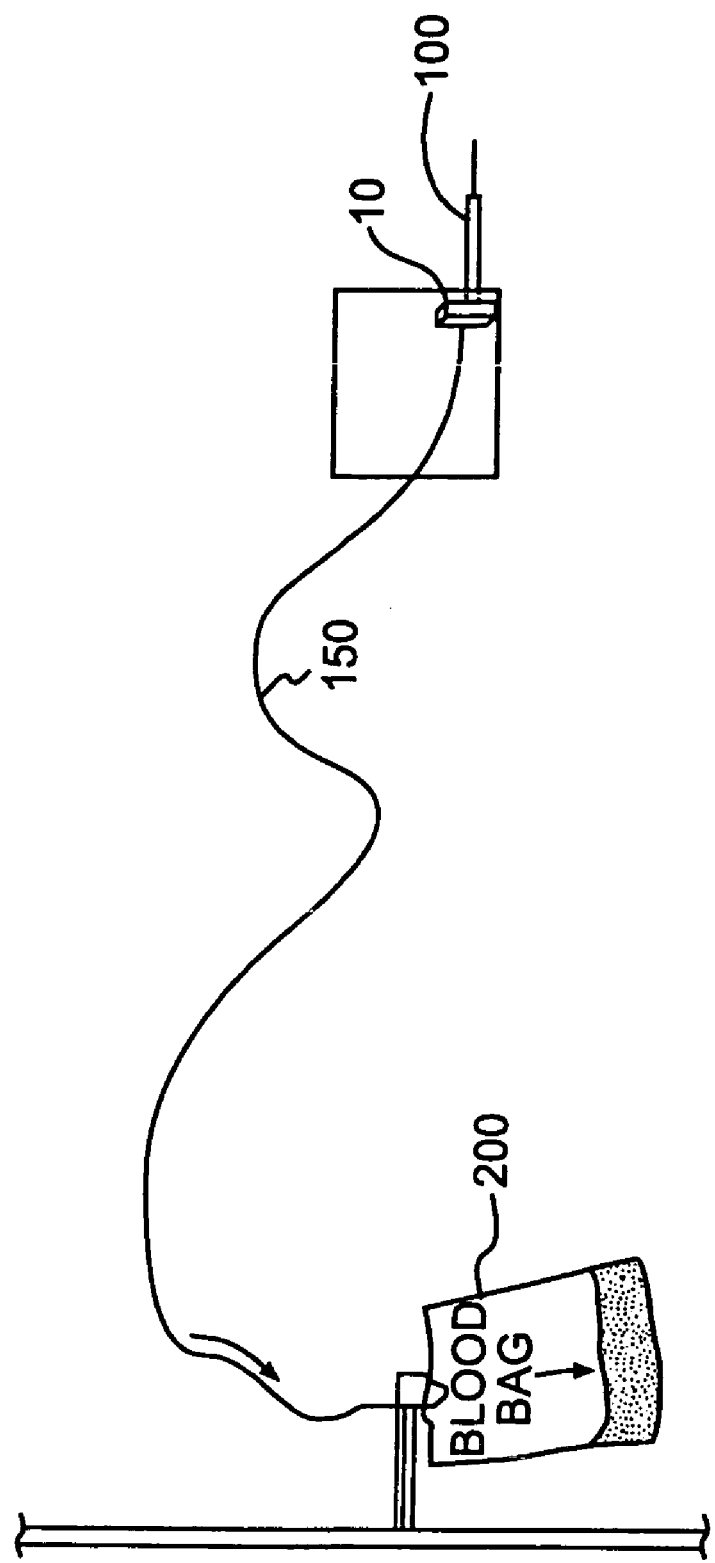
FIG. 1A shows one embodiment of the invention as a self-contained screening capture device (10) as part of the blood collection system from the patient to the blood collection bag.

The present invention relates to a system for screening blood and to several components of a blood screening system, including screening capture devices, capture systems, amplification systems and detection systems for target agents or components of interest. The system is designed to detect target agents and molecules associated with or indicative of a disease, a condition or contamination in blood. Target agents and molecules may be associated with pathogens, including viruses, bacteria, fungi and prions. Such target agents and molecules include HIV (human immunodeficiency virus) and associated proteins, such as GP120, P24 core, P55 core and P31, and fragments thereof; HBV (hepatitis B virus)and associated proteins, such as core, HbeAg, HbsAg, S1 and S2 and fragments thereof; and HCV (hepatitis C virus) and associated proteins, such as core (C22), envelope (E1E2), and NS3, NS4 and NS5, and fragments thereof; nucleic acid molecules, such as HCV (such as in the NTR region), HIV (such as LTR region or pol gene region), and HBV (such as preS1/2 and S region). Additionally, the target agents further include parvovirus B19, HGV (GBV-C), TTV, SEN-V, HHV-8, nvCJD, vCJD (prion), Plasmodium species, the causative agent of malaria, Flavivirus species, the causative agents of West Nile virus, St. Louis encephalitis, Japanese encephalitis, yellow fever virus, Dengue virus. Further, target agents and molecules include blood components or factors, such as ABO, RhD factor, and irregular red cell antibodies. The system employs recombinant proteins for antibody detection, monoclonal and polyclonal antibodies for antigen detection, and nucleic acids for nucleic acid detection.

Screening Capture Device Design

As noted, the invention provides a screening capture device for in-line screening of blood that is collected using a collection needle connected by a collection duct to a collection bag. "In-line" screening refers to the ability to screen blood as it is collected from a donor, and is possible by the use of a flow-through screening capture device. Accordingly, the inventive screening capture device comprises a case having an inlet for blood collected from the collection needle and an outlet that drains the blood from the screening capture device to the collection duct; the case houses a biochip unit that captures target agents or molecules from the blood. In one embodiment the inlet of the screening capture device is directly connected to the rear end of the collection needle, meaning that the screening capture device is connected distal to the end of the collection needle that is inserted into the donor. Alternatively, the inlet of the screening capture device is connected, via a collection duct, proximate to the collection needle, so the temperature of blood in the screening capture device is approximately 37° C. In still other embodiments, the screening capture device is located at an inlet of the blood collection bag or even inside of the bag.

In one embodiment, the biochip unit of the screening capture device contains a first biochip and a second biochip that are sequentially arranged between the inlet and the outlet, such that blood first flows across the first biochip, then flows across the second biochip. In such an arrangement, the biochips may be arranged end-to-end, side-to-side, or in a parallel stacked fashion. Alternatively, the biochips may be arranged non-sequentially. Preferably, the dimensions of the screening capture device are designed such that a flow rate of blood flowing through the screening capture device is roughly equal to the flow rate of collected blood in the absence of the screening capture device. In one embodiment, the dimensions of the screening capture device are designed such that the flow rate of the blood flowing through the screening capture device is roughly 450 ml per 10 minutes. The screening capture device also is preferably designed such that the dimensions of the inlet, the outlet, the surface area of biochips in the biochip unit, and the screening capture device case allows the collected blood to maintain a constant flow rate through the screening capture device. The outlet optionally includes a funnel and a filter. In one embodiment, the screening capture device further comprises an anti-backflow device that prevents the blood from flowing back towards the inlet. In a further embodiment, the inlet and outlet are designed to be sealed when the screening capture device is removed from the collection needle and the collection duct. Various means for sealing the inlet and outlet can be employed, including plugs, caps, heat seals, clamps, welds and so forth.

As used in the description of this invention, "biochip" refers to a device comprising a substrate that incorporates one or more analytes, or biological recognition components. For example, biochips include measurement devices that incorporate an analyte into or with devices that are prepared using microlithography or microarraying technologies. Analytes include DNA, RNA and proteins (including enzymes, antibodies, receptors and their functional fragments and biomimetic equivalents), subcellular organelles, cells and tissues. The "biochip" can take any form that provides a substrate for incorporating analytes. Thus, biochips may be in the form of a chip, a bead, a gel, a microparticle, a membrane, a slide, a plate, a pellet, a disk, a capillary, a hollow fiber, a needle, a solid fiber or another form capable of providing a substrate for capturing target agents or molecules.

Biochips may comprise a wide variety of compositions, including glass, plastic, silicon, alkanethiolate-derivatized gold, cellulose, low crosslinked and high crosslinked polystyrene, silica gel, polyamide, and the like.

Biochips preferably are capable of supporting a microarray. The term "microarray" refers to the panel of analytes, or biological recognition components, used for testing, and to the panel's ordered two-dimensional presentation on a biochip. "Low density biochips" contain microarrays of less than 100 analytes. "Medium density biochips" contain microarrays of 100 to 1000 analytes. "High density biochips" contain microarrays of more than 1000 analytes.

The inventive screening capture device is used to capture, on a biochip, one or more target agents or molecules comprising at least one protein or nucleic acid molecule, or a fragment thereof, indicative of or specific for a disease or an infectious agent. The target agents or molecules may be antigens, including viral proteins, bacterial proteins, prion proteins, antibodies, and antigen-antibody complexes; whole bacterial cells; whole fungal cells; whole viruses; or nucleic acids, particularly DNA. For capturing targets, the biochip contains analytes, or biological recognition components, that bind to the target agents or molecules. These analytes may be proteins, including antigens and antibodies, small peptides, oligonucleotides, lectins, small organic molecules, inorganic metallo-complexes, ions, modified peptides or peptidomimetics. The selection of particular analytes for binding particular target agents or molecules is well within the skill or ordinary artisans in this field.

The first biochip of the screening capture device is a nucleic acid amplification technique (NAT) biochip, on which multiple assays may be run. The first biochip captures at least one infectious organism or cell containing a targeted nucleic acid molecule. The infectious organism may be a virus, bacteria, fungi, protozoan, mycoplasma or prion. The cell is a cell from the donor of the blood sample. The first biochip will contain one or more analytes for capturing target agents or molecules. These analytes may be proteins, including antigens and antibodies, small peptides, oligonucleotides, lectins, small organic molecules, inorganic metallo-complexes, ions, modified peptides or peptidomimetics. The analytes should possess high binding affinity for target agents or molecules, and should not leach out to blood. Multiple analytes with different chemical natures may be employed on the same biochip to achieve simultaneous capturing and screening for multiple targets.

The second biochip of the screening capture device is an immunoassay chip, on which multiple assays may be run. The second biochip captures targeted antigens and/or antibodies. The second biochip also will contain one or more analytes for capturing target agents or molecules. These analytes also may be proteins, including antigens and antibodies, small peptides, oligonucleotides, lectins, small organic molecules, inorganic metallo-complexes, ions, modified peptides or peptidomimetics. The analytes should possess high binding affinity for target agents or molecules, and should not leach out to blood. Again, multiple analytes with different chemical natures may be employed on the same biochip to achieve simultaneous capturing and screening for multiple targets.

In one embodiment, the first and second biochips are low density biochips. In a further embodiment, the first and second biochips are microarrays having the analytes that bind to target agents or molecules arranged along the length of the biochip in the direction of blood flow over the first and second biochips, respectively. Analytes preferably are covalently bound to the biochips.

Rather than containing two biochips, the screening capture device alternatively may contain a single first biochip that is a NAT biochip or is an immunoassay chip or constitutes both an NAT biochip and an immunoassay chip. For example, a biochip that captures whole pathogens can be used to detect both antigen targets, by immunoassay detection techniques, and nucleic acid targets, by NAT detection techniques.

The surface of biochips used in the invention may be composed of any material that that allows covalent attachment of nucleic acids and/or proteins, preferably at a high density. Exemplary materials are glass, quartz, plastics, biopolymers and semiconductor nanocrystals, such as Quantum dots or Quantum Beads. Any of these materials may have surface modifications to enhance their performance.

In some embodiments, the screening capture device comprises one or more semi-permeable membranes that insulate cellular components of the blood from the biochip, where binding events between biological recognition components and target agents or molecules occurs. Such membranes are permeable to target agents and molecules, but not to blood cells. To protect the integrity of cellular components in blood, the membranes may be positioned upstream of a biochip or may entirely envelop a biochip. The membranes may operate based on size exclusion or other functional principles. Selection of a particular membrane is dictated by purpose. For example, membranes comprising a pore size of between 500 angstroms and 5 microns, preferably about 1 micron, will allow viral particles and target molecules to pass, but not blood cells.

One or more semi-permeable membranes also may be employed to prevent materials from leaching out from the screening capture device into the collected blood. Used in this context, the semi-permeable membranes permit cells to pass, but not proteins or small molecules. To protect collected blood from materials leaching out of the screening capture device, the membranes may be positioned downstream of a biochip or may entirely envelop a biochip.

The screening capture device additionally may comprise a lid that can be robotically removed to facilitate sequential robotic removal of the first biochip and the second biochip.

In one embodiment, the screening capture device of the invention accommodates biosensors capable of supporting a "self-performing" screening assay. For example, engineered B-cells with surface antibodies specific for target agents or molecules may be attached to the biochip. The engineered B-cells express cytosolic aequorin, a calcium-sensitive bioluminescent protein from *Aequoria Victoria* jellyfish. Once a target binds to the B-cell, it will trigger an elevated intracellular calcium concentration, which will illuminate aequorin. See, e.g., Rider et al., Science, 301: 213-215 (2003). A "self-performing" screening assay is particularly advantageous when the screening capture device is located inside of a blood bag, because the assay results can be determined without opening the bag and thereby potentially contaminating its contents. It also allows for continuous monitoring of a blood sample, such that pathogens growing over time can be detected.

In another aspect, the invention provides a screening system for in-line screening of blood collected using a collection needle connected by a collection duct to a collection bag. The screening system comprises a screening capture device as described herein and at least one biochip processor for amplifying and/or detecting at least one captured target agent or molecule. The screening system may contain multiple biochip processors.

In one embodiment, the biochip processor of the screening system comprises a sealed disposable unit having a nucleic acid amplification technique (NAT) portion for processing a biochip and/or an immunoassay portion for processing a biochip.

For detecting nucleic acid target molecules, the NAT portion of the biochip processor may comprise a biochip holder, one or more reservoirs for holding an eluted or lysed target agent or molecule, i.e—a sample, one or more amplification reaction chambers connected to the reservoir, and one or more detection components connected to the amplification reaction chamber. The NAT portion may further comprise one or more reagent containers connected to the reservoir and one or more reagent containers connected to the reaction chamber. The NAT portion may further comprise a biochip held in the biochip holder. In one embodiment, the biochip is held such that the analytes are in contact with at least one elution and lysing buffer. The detection component of NAT portion of the biochip processor may comprise one or more microfluidity chambers.

For detecting antibody and/or antigen target molecules, the immunoassay portion of the biochip processor may comprise a biochip holder, one or more reservoirs for holding an eluted or lysed target agent or molecule, i.e.—a sample, one or more reaction chambers connected to the reservoir, and one or more detection components connected to the reaction chamber. The immunoassay portion may further comprise one or more reagent containers connected to the reservoir and one or more reagent containers connected to the reaction chamber. The immunoassay portion may further comprise a biochip held in the biochip holder. In one embodiment, the biochip is held such that the attached analytes are in contact with at least one buffer. The detection component of the immunoassay portion of the biochip processor may comprise one or more microfluidity chambers. The biochip processor generally comprises at least two reaction chambers, one for the detection of a target antibody and one for the detection of a target antigen. The biochip processor is designed so that each reaction chamber is connected to at least one detection component comprising one or more microfluidity chambers.

In a related aspect, the invention provides methods of screening blood collected from a donor by using a collection needle connected by a collection duct to a collection bag. The methods employ the screening capture devices and screening systems described herein. One method comprises the following steps: (a) providing a screening capture device comprising: an inlet for blood collected from a collection needle, a biochip unit that captures a target agent or molecule from collected blood, and an outlet that drains the blood from the screening capture device to a collection duct; (b) inserting the screening capture device between the collection needle and the collection duct proximate to the collection needle so that blood flowing through the screening capture device is approximately at a human body temperature, and (c) allowing blood to flow through the screening capture device. The method may further comprise (d) removing the sealed screening capture device for further processing of the biochip unit.

In some embodiments, the method further comprises (a) opening the screening capture device to remove the biochip unit, and (b) inserting the biochip unit into a biochip processor for processing. These steps may be performed robotically.

When a target molecule is a nucleic acid, the biochip processor comprises a nucleic acid amplification technique (NAT) portion for processing the biochip. This NAT portion may comprise a biochip holder for holding the biochip, one or more reservoirs for holding a sample eluted from the biochip, one or more amplification reaction chambers connected to the reservoir, and one or more detection components connected to the amplification reaction chamber. The NAT portion may further comprise one or more reagent containers connected to the reservoir.

In such cases, the method further comprises contacting the biochip with at least one buffer from the reagent container that elutes and lyses the captured target agents and molecules from the biochip to form a solution that collects in the reservoir. The method further comprises moving a solution in the reservoir to the amplification reaction chamber, providing one or more reagent containers that contain nucleic acid amplification reagents and allowing the amplification reagents to flow into the amplification reaction chamber containing the solution, providing sufficient conditions to amplify at least one nucleic acid molecule in the solution, and detecting the presence of the amplified nucleic acid molecule in the detection component. In one embodiment, the detection component comprises one or more microfluidity chambers for detecting the presence of an amplified nucleic acid molecule by a nucleic acid hybridization and signal detection. More than one biochip processor may be utilized in parallel.

When the target molecule is an antibody or antigen, the biochip processor comprises an immunoassay portion for processing the biochip. This immunoassay portion may comprise a biochip holder, one or more reservoirs for holding a sample eluted from the biochip, one or more reaction chambers connected to the reservoir, and one or more detection components connected to the reaction chamber. The immunoassay portion further comprises one or more reagent containers connected to the reservoir.

In such cases, the method further comprises contacting the biochip with at least one buffer from the reagent container that elutes the captured target molecules from the biochip to form a solution that collects in the reservoir. The method further comprises moving the solution in the reservoir into the one or more reaction chambers, providing one or more additional reagent containers that contains a reagent comprising an antigen linked to a signal amplification system or an antibody linked to a signal amplification system and allowing the reagent to flow into the reaction chamber containing the solution, providing sufficient conditions to allow binding of the reagent to a target antibody or antigen in the solution, and detecting the presence of the target antibody or antigen in the detection component. In one embodiment, the method utilizes a detection component that comprises one or more microfluidity chambers for detecting the presence of the signal by binding to an antibody immobilized on the wall of the chamber. In one embodiment, the method employs least two reactions chambers, one for the detection of a target antibody and one for the detection of a target antigen. Each reaction chamber is connected to at least one detection component comprising one or more microfluidity chambers. Also, more than one biochip processor may be utilized in parallel.

Reference to the figures will provide a more complete understanding of the screening capture devices and screening systems. As shown in FIG. 1A, the invention provides a self-contained screening capture device (10) that is removable and preferably secured between a collection needle (100) and a collecting duct (150) that transfers collected blood to a collection receptacle or container, for example, a blood bag (200). FIG. 1A is exemplary only, and one skilled in the art would recognize various alternatives and improvements, which the invention also embraces. The screening capture device (10) is preferably located close to the donor of the blood, preferably connected directly to the collection needle (100) (for example, near or at the back end of the needle) to ensure that the temperature of the blood is still close to 37° C. or an appropriate temperature for effective capture of target agents or components of interest (for example, antigens/antibodies and nucleic acid complexes).

Figure 1B:
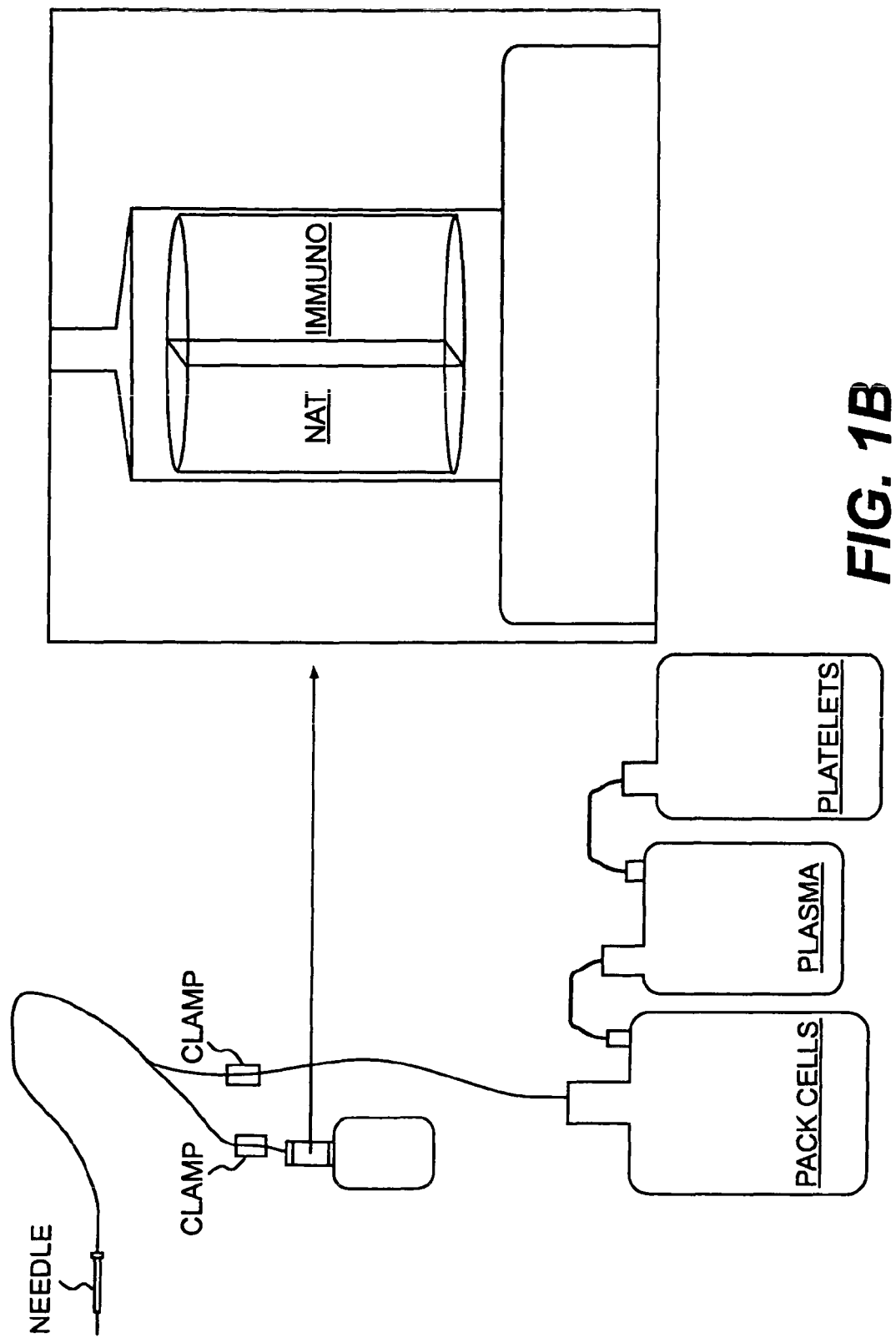
FIG. 1B illustrates an alternate embodiment, in which the screening capture device containing one or more biochips is located within the neck of a diversion blood collection bag.

In an alternative arrangement, as shown in FIG. 1B, the screening capture device may also be located within the blood bag (200). This arrangement is particularly advantageous in a system in which the blood from a donor is collected in multiple blood bags. In such a system, the screening capture device can be arranged inline with a first bag or diversion bag that collects the initial blood collected from a subject. For example, 10-40 ml may be collected in the first bag. The first bag may then be removed or bypassed so that the remainder of the collected blood is stored in one or more additional blood bags. The bag containing the biochip may then be placed on a slow shaker to maximize contact of the biochip with blood.

This multiple bag configuration, with the biochip contained in the first bag that collects blood, provides several advantages. First, potential bacterial contamination from the skin of the blood donor may be collected in the first bag so that the second and subsequent bags are free from or have reduced bacterial contamination. Second, the biochip(s) contained in-line with the first bag, by being located in the top of or inside of the first bag, may be kept in contact with the blood for a longer duration of time at any desired temperature before elution and testing.

One of skill in the art would recognize that the principles of arranging the biochip(s) in the first bag can also be extended to placing biochips in the first few bags that collect blood if different processing or analysis is desired for the biochip(s) in the separate bags. For example, biochips may be placed in the first two or more bags, with additional blood being collected in one or more additional bags after the first two or more bags have been sequentially disconnected or bypassed.

Figure 2:
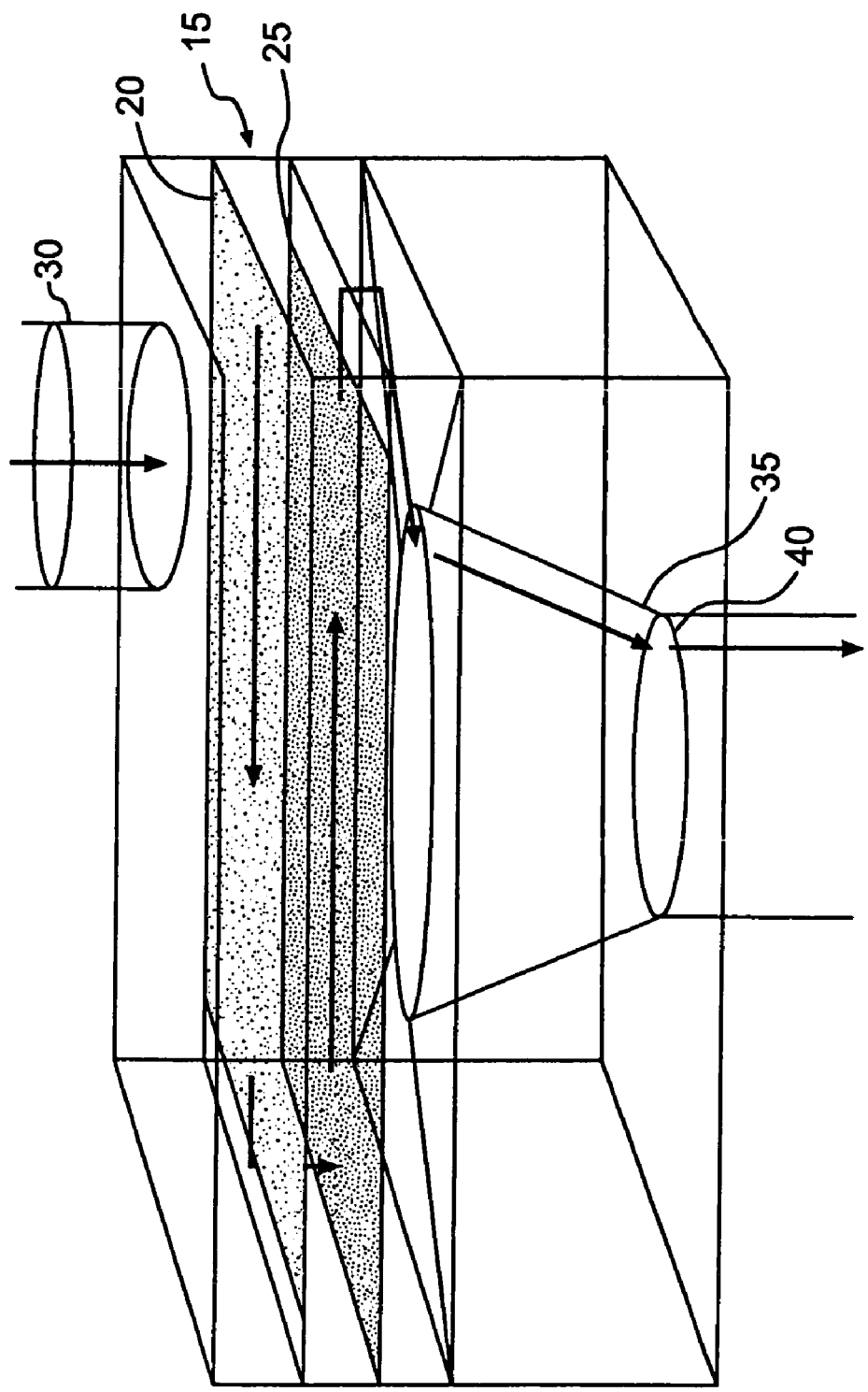
FIG. 2 illustrates a more detailed view of the screening capture device (10) in relation to the blood inlet 30 and the funnel (35) and filter (40) as the blood drains from the filter into the collecting duct.

As shown in FIG. 2, in one embodiment, the screening capture device (10) is designed as a small box that contains an inlet (30), a biochip unit (15) (shown having two biochips (20) and (25)), and a funnel (35) with a filter (40) at the bottom. FIG. 2 is exemplary only and one skilled in the art would recognize various alternatives and improvements, which the present invention also encompasses. Blood will flow from the collection needle (100) through the collecting tube (150) and then through the chambers of the screening capture device (10), and out of the bottom of the screening capture device (10) (via the funnel (35)), into the blood bag (200). As an alternative, the screening capture device (10) may be directly connected to the collection needle (100) (for example, at a rear end thereof) so that the collected blood flows directly from the collection needle (100) to the screening capture device (10) before entering the collection duct, or tube, (150) for transmission to the blood bag (200).

Preferably, the screening capture device (10) is removably attached to the collection needle (100) or the collection duct (150) so that the screening capture device (10) can be removed for further processing after blood is collected. Furthermore, the screening capture device (10) is attached to the collection needle (100) or the collection duct (150) as close as possible to the blood donor so that blood flowing through the screening capture device (10) is as close as possible to a human body temperature (roughly 37° C. or 98.6° F.).

As shown in FIG. 2, preferably a first biochip (20) lays securely suspended in a plane parallel to and above a second biochip (25). Below the second biochip (25), is arranged a funnel (35) and a filter (40), preferably with pores around 100 to 200 microns, that allow blood to flow out of the screening capture device (10) into a collection duct (150) that is connected to the blood bag (200). As blood enters the removable screening capture device (10), which is completely sealed prior to removal, it is forced to flow across the entire surface of first biochip (20). As the blood reaches the end of first biochip (20), it cascades down to the second biochip (25) and flows along the surface of the second biochip (25). After flowing along the surface of the second biochip (25), the blood then cascades down to the funnel (35) and filter (40), and then onto the collection duct (150) and the blood bag (200). One skilled in the art would recognize that the collection duct (150) is only provided so that the blood bag (200) may be located at a suitable position. Alternatively, the screening capture device (10) may be directly connected to the blood bag (200). The funnel (35) and the filter (40) are preferably encased in the lower portion of the screening capture device (10), which preferably is shaped as a box-shaped device. Anti-coagulants and other additives are provided in the blood bag (200), as is known to those skilled in the art. Additionally, conventional or known anti-backflow devices may be installed at several locations in the blood flow path that includes the collection needle (100), the screening capture device (10), the collection duct (150), and the blood bag (200).

The screening capture device (10) may be removed from the collection needle (100) or the collection duct (150) after blood collection from a donor has been completed. This can be accomplished, for example, by thermally sealing the inlet and the outlet of the screening capture device (10). The screening capture device (10) can then be removed for further processing and analysis of the biochips.

In addition to the "tandem" arrangement of the two biochips, the present invention also contemplates that more than two biochips may be arranged in tandem. Furthermore, in an alternate embodiment, the present invention contemplates that a single biochip, for example, a single "cylindrical" biochip may be used instead. In this cylindrical biochip embodiment, for example, one half of cylindrical biochip could be used for the NAT assay while the other half of the cylindrical biochip could be used for the immunoassay (see FIG. 1B). The size and dimensions of the biochips should be designed to maximize contact between the blood sample and the surface of the biochip. When using a single biochip, a different (more harsh) elution is used for the nucleic acids tested while a less harsh elution is used for the antigens and antibodies tested. One of the skill in the art would also recognize that while the embodiment discussed herein discloses the NAT assay biochip as the first biochip and the immunoassay biochip as the second biochip, the relative arrangement of the biochips are interchangeable.

Figure 3:
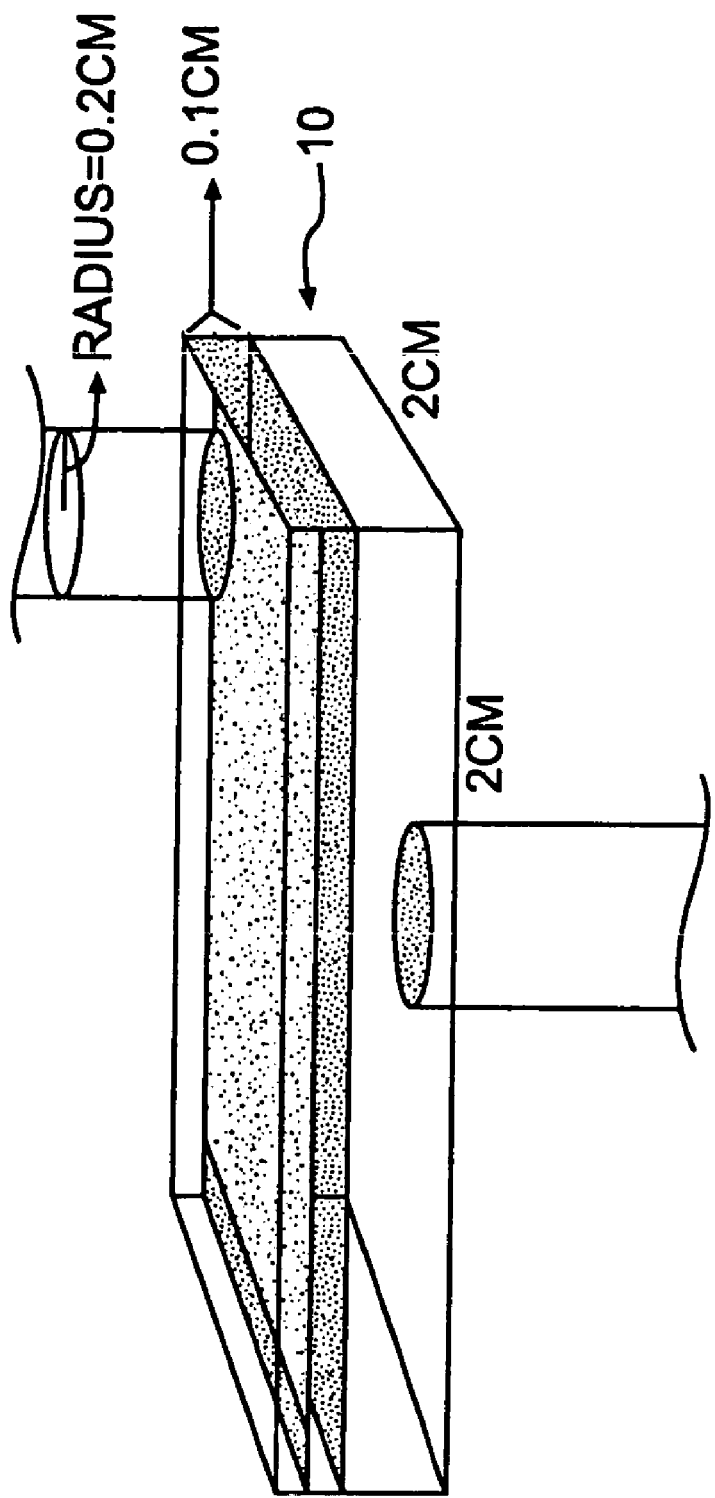
FIG. 3 illustrates one example of the various dimensions of the components of the screening capture device (10).

The current apparatus used to collect blood typically yields a collection rate of about 450 ml, or one pint, per 10 minutes. To maintain this flow rate or a similar desired flow rate, the dimensions of the screening capture device (10) are designed so that it does not slow down the flow of blood. Thus, the screening capture device's (10) chambers through which the blood flows are designed to have a cross-sectional area that is no smaller than that of the commonly used collection tube. In addition to this requirement, the height of the chambers should be minimized, and the surface area dimension corresponding to biochip surface area that contacts the blood should be maximized, to enhance the fraction of blood that contacts the biochips in the screening capture device (10). As one example, given an estimated radius of 2 mm for the commonly used collection tube and a desired chamber height of 1 mm, calculations yield a proposed width of 2 cm and length of 2 cm for the biochips. FIG. 3 illustrates one example of the various dimensions of the components of the screening capture device (10) in order that the blood flow through the screening capture device (10) is no slower than the flow through the collection tubes (150) in the absence of the screening capture device (10). One skilled in the art would recognize that various dimensions of the screening capture device (10) and its components can be determined based on the design principles disclosed herein and all such dimensions are considered to be a part of the present invention.

Capture Design

The purpose of the biochips (20), (25), in the screening capture device (10) is to capture target disease agents or components or metabolic molecules from the blood. For example, these target agents or components include viruses, cells, proteins, such as antibodies, antigens or other proteins that are indicative or specific for a disease agent, and other molecules that are indicative or specific for a disease agent or disease condition, contained in the blood. Preferably, the biochips (20), (25) provide both a qualitative and quantitative readout of the identity and level of target agents or components in the blood. In one embodiment, the first biochip is a NAT (nucleic acid amplification technique) system, while the second biochip (25) is an immunoassay chip. Therefore, the first biochip (20) will capture viruses or cells that contain at least one nucleic acid molecule or nucleic acid complex, associated with disease agents, e.g., viral or bacterial nucleic acid molecules. The captured cells may possess a viral epitope on the cell surface or these cells may be of a type that are targeted by viruses and can be identified by a specific cell surface marker. The second biochip (25) will capture viruses, cells, proteins and/or viral/protein complexes and detect proteins, such as antibodies to specific target disease agents or components or specific target disease antigens that are recognized and bind to a corresponding antibody. Preferably, both the first and second biochips are medium- or low-density chips, each with space for the immobilization of several hundred analytes that function as potential binding moieties to the target agents and molecules. These analytes may be spotted onto the respective biochips by a robotic spotting device.

The first and second biochips described above may be combined into a single biochip capable of supporting an NAT and an immunoassay detection system.

Figure 4A:
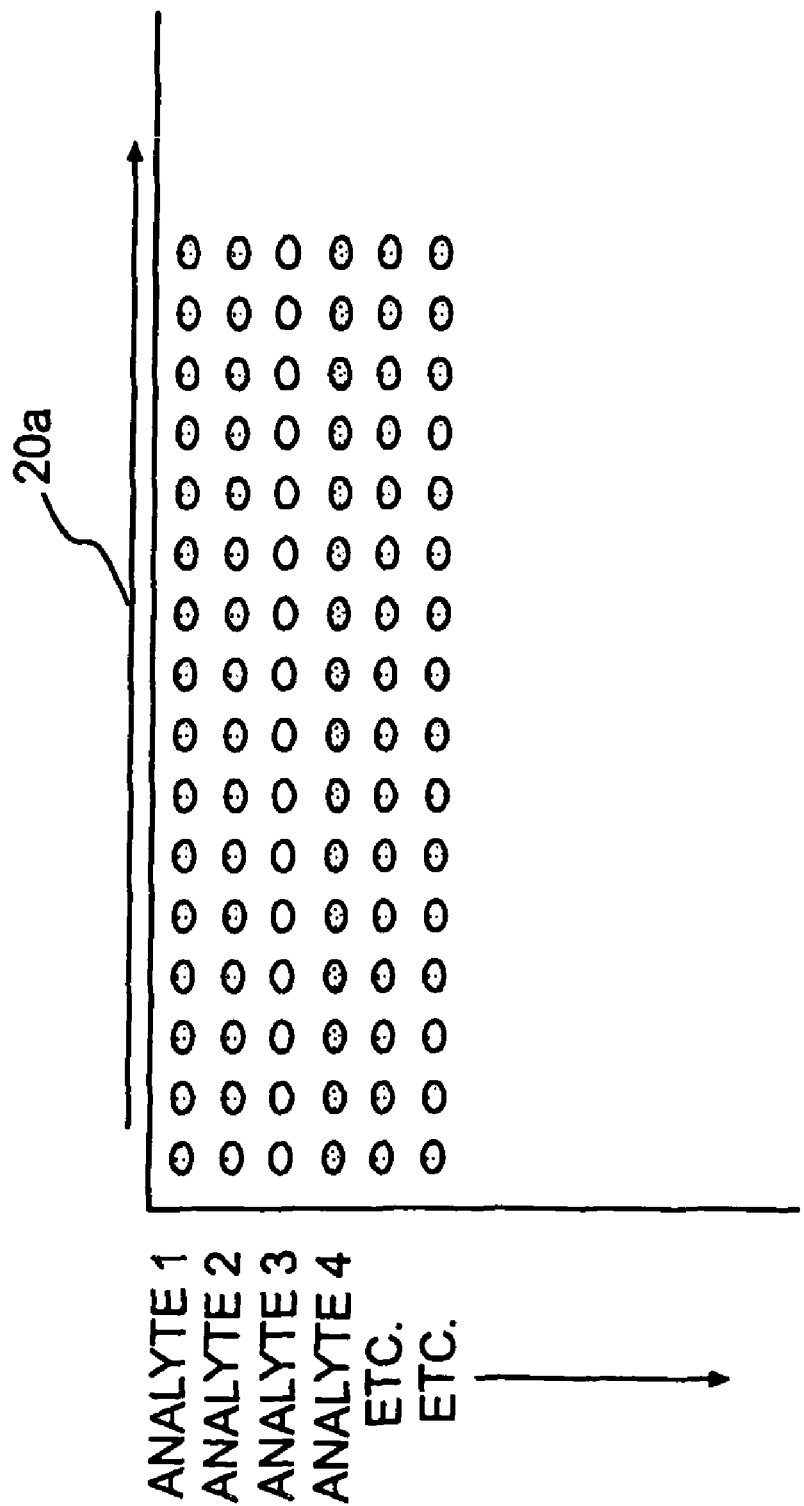
FIG. 4A illustrates an arrangement of different analytes on a three dimensional matrix in a latitudinal (in the direction of blood flow 20a) linear fashion.
Figure 4B:
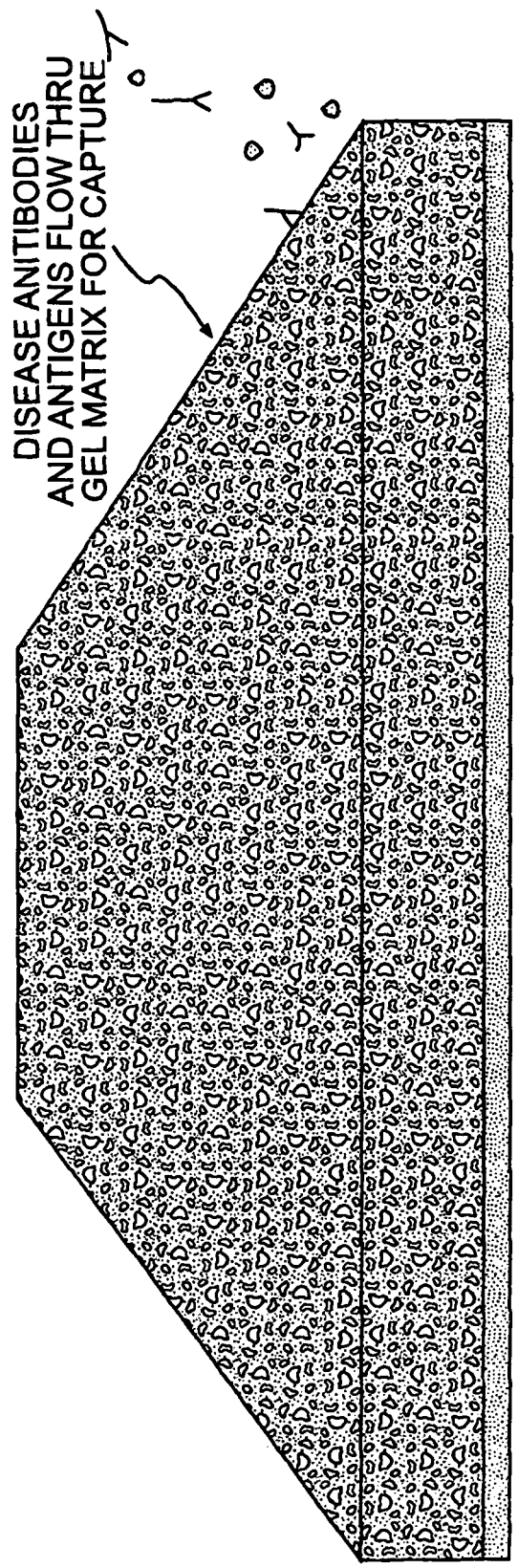
FIG. 4B shows a three-dimensional matrix using Hypogel technology that enhances the space for conjugation/capture and sensitivity.
Figure 4C:
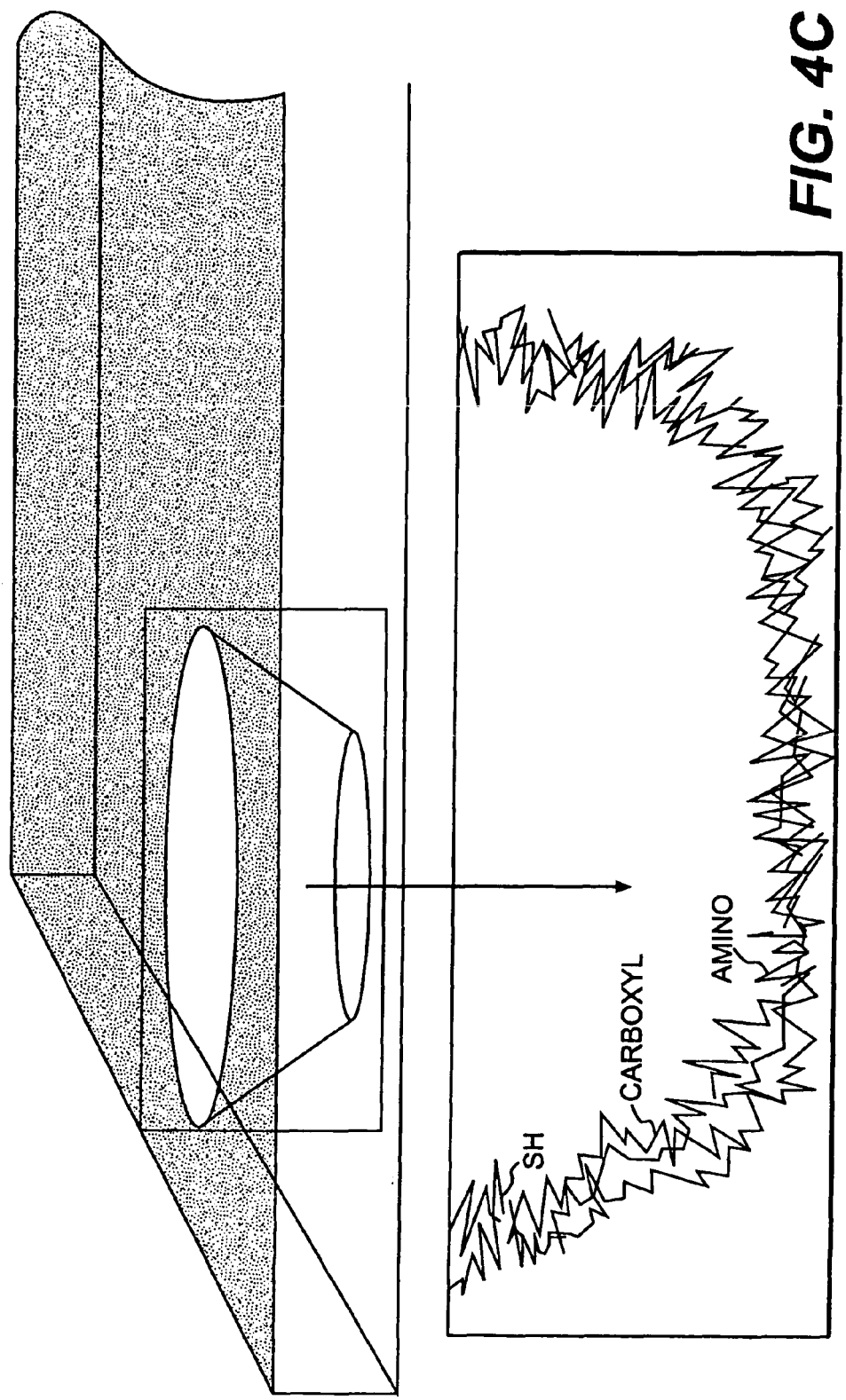
FIG. 4C shows a three-dimensional matrix as a glass biochip with wells containing villi-like protrusions.
Figure 4D:
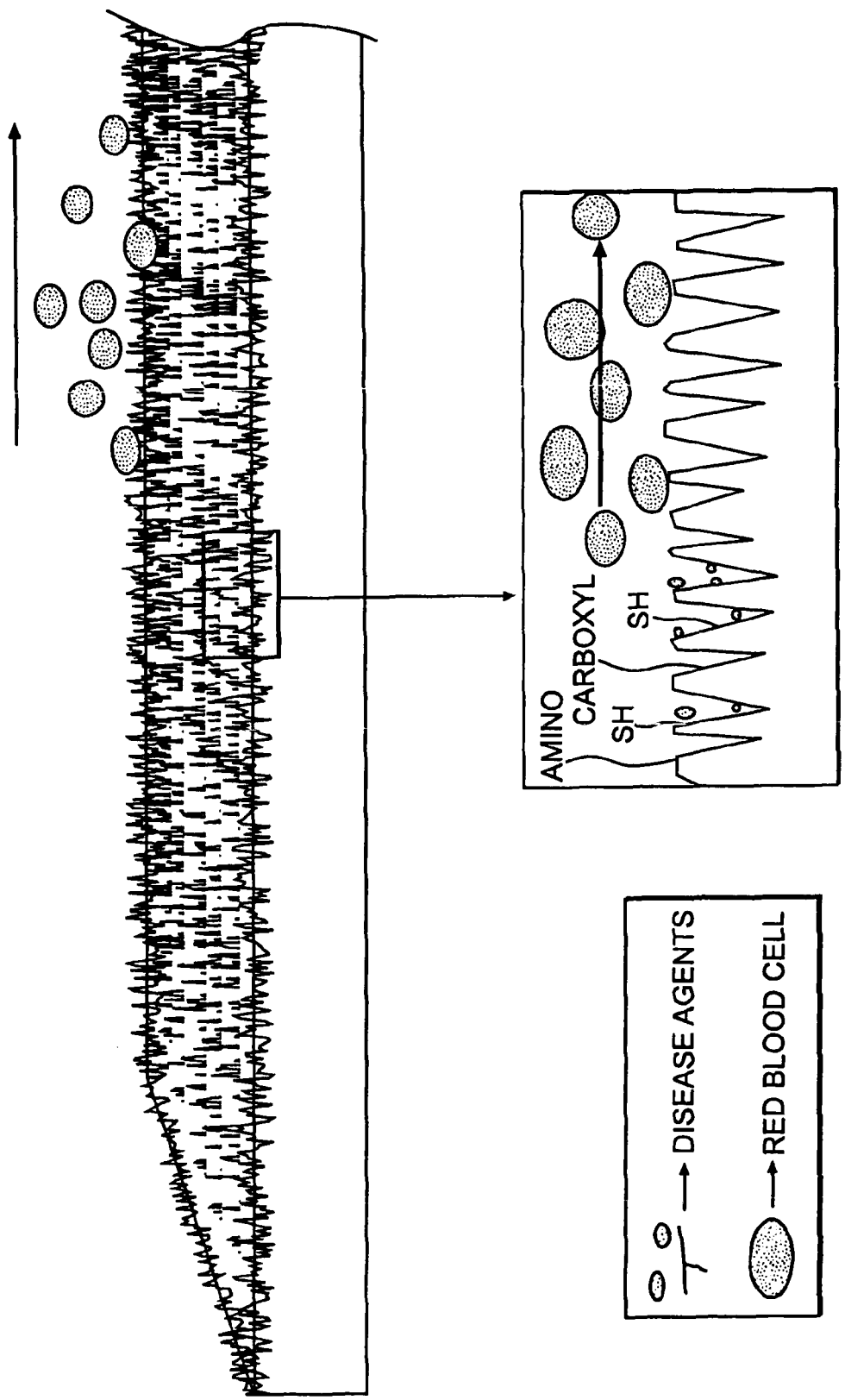
FIG. 4D shows another embodiment of a glass biochip in which the entire surface of the biochip is rough with villi-like protrusions.

In one embodiment, as shown in FIG. 4A, different analytes are spotted on microarray slides in a latitudinal linear fashion, in the direction of blood flow 20a, so that every analyte covers the entire length of the biochip (20), to maximize biochemical interaction or binding between the target agent or component of interest in the blood and the latitudinally arranged analyte microarray. Thus, one of the features of the present invention is that multiple spots are provided for detecting particular analytes so that even non-homogeneously distributed analytes may be detected. As shown in FIG. 4A, therefore, the respective probe elements of the analytes of interest are latitudinally, or linearly arranged on the biochip in the direction of blood flow 20a across the biochip (20). Preferably, the binding surface will be three-dimensional to increase binding capacity. For example, currently available three-dimensional biochips in gel format may be used, provided that the leaching is minimized. Therefore, the surface selected preferably is a three-dimensional solid surface that provides more surface area and more binding capacity, with minimized leaching from the surface. Examples of such surfaces are plastic, silicon, rubber and resins. On the surface, functional groups may be attached by chemical linking to allow for different binding chemistry to occur with disease agents. The surface mesh preferably has spaces that are submicron in size to avoid catching red blood cells. Commercially available HypoGel (Sigma-Aldrich Corp., St. Louis, Mo.) is one example of a three-dimensional binding surface, such as shown in FIG. 4B, and provides a three-dimensional matrix that enhances the space for conjugation/capture as well as increases the sensitivity. HypoGel® is a hydrophilic polystyrene gel-type resin. Based on a low crosslinked (1% DVB) polystyrene matrix, oligo ethylene glycols are grafted to form a high loaded hydrophilic resin. The reactive centers are located at the terminus of the glycol spacers. NMR measurements indicate their high flexibility. A glass chip with similar capabilities to the Hypogel may be designed to maximize the capture of disease agents, as shown in FIGS. 4C and 4D. FIG. 4C shows a glass biochip with wells. The surface in the wells are rough with small protrusions to maximize surface area and binding capacity. FIG. 4D shows another embodiment of a glass biochip in which the entire surface of the biochip is rough with villi-like protrusions. The villi-like protrusions enhance the surface area for binding and form a mesh-like surface with sub-micron size spaces in-between. The material of the biochip should be selected to maximize the binding surface to increase binding capacity, without resulting in leaching of the bound target molecules to the surrounding bio-fluidic environment.

Figure 5:
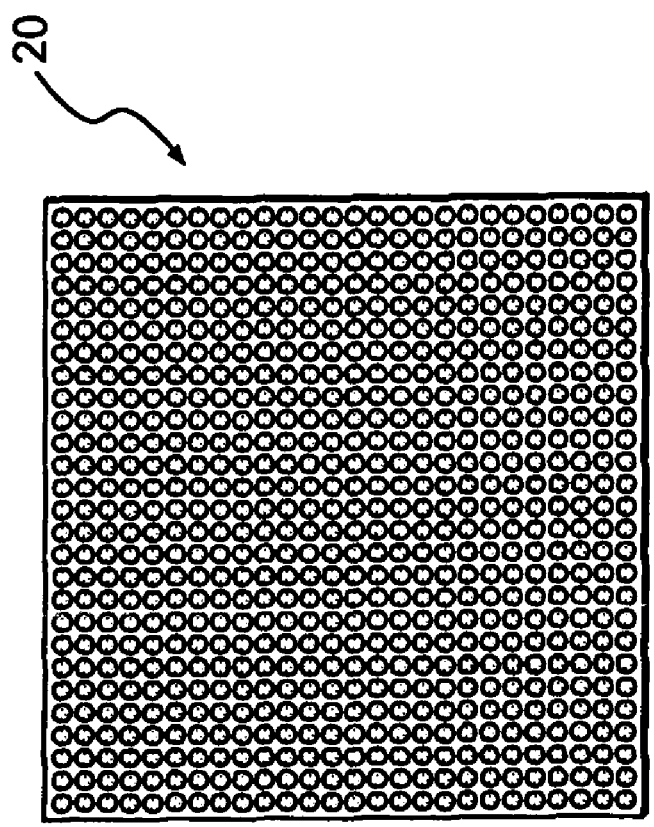
FIG. 5 shows one example of a biochip (20) produced by Rockefeller University's Gene Array Resource Center that is designed for performing a NAT system assay.

FIG. 5 discloses one example of a biochip (20) produced by Rockefeller University's Gene Array Resource Center that is designed for performing a NAT system assay that spots the analytes listed in box 22 below. The specific analytes disclosed in box 22 include antibodies for capturing the antigen and nucleic acid complexes, while the only nucleic primers disclosed for NAT capture are from the NTR region for HCV and the LTR region for HIV.

| Box 22 Analytes to be Spotted on the Biochip | | |
|---|---|---|
| HCV: | mAb against core (C22) mAb against NS3, NS4, NS5 | MAb against env E1E2 |
| HIV: | mAb against GP120 mAb against P55 core | mAb against P24 core mAb against P31 |
| HBV: | mAb against core mAb against HBeAg | mAb against HBsAg mAb against S1 and S2 |
| Also, nucleic acids themselves maybe spotted for hybridization | | |
| HCV: | 5' endNTR | |
| HIV: | LTR region | Pol gene region |
| HBV: | preS½ and S region | |

To protect collected blood from contamination by analytes immobilized on the biochips (20), (25), the antigens coated on the second biochip (25) are preferably attached covalently. Also, with respect to the biochip material used as well as the material used for the remaining components of the screening capture device (10), surface considerations with respect to flow and contamination are considered to maximize the blood flow across the various surfaces of the screening capture device (10) while minimizing or preventing contamination of the blood flowing therethrough. Factors such as analyte array element density and purity, substrate attachment and biological activity of the material should be considered to conform to the needs of a particular blood collection project and to ensure protection of the blood from alterations or adulteration. For example, Versalinx chemistry may be used to conjugate the proteins and the nucleic acids on the biochips, to minimize leaching of the analytes into the blood stream and into blood collected in the blood bag. Versalinx is a chemical affinity tool made by Prolinx Company, Bothwell, Wash. The Versalinx protein microarray technology is based on interaction of synthetic molecules that allow the formation of a stable complex to immobilize proteins, peptides and nucleic acids onto solid surfaces. Another solution to this problem, as discussed earlier, involves using a first bag or a diversion bag with the biochip(s) to collect the initial flow of blood from a donor before the first bag is disconnected or bypassed, so that the blood can flow directly into a second or additional blood bags without flowing over the biochip.

Figure 6:
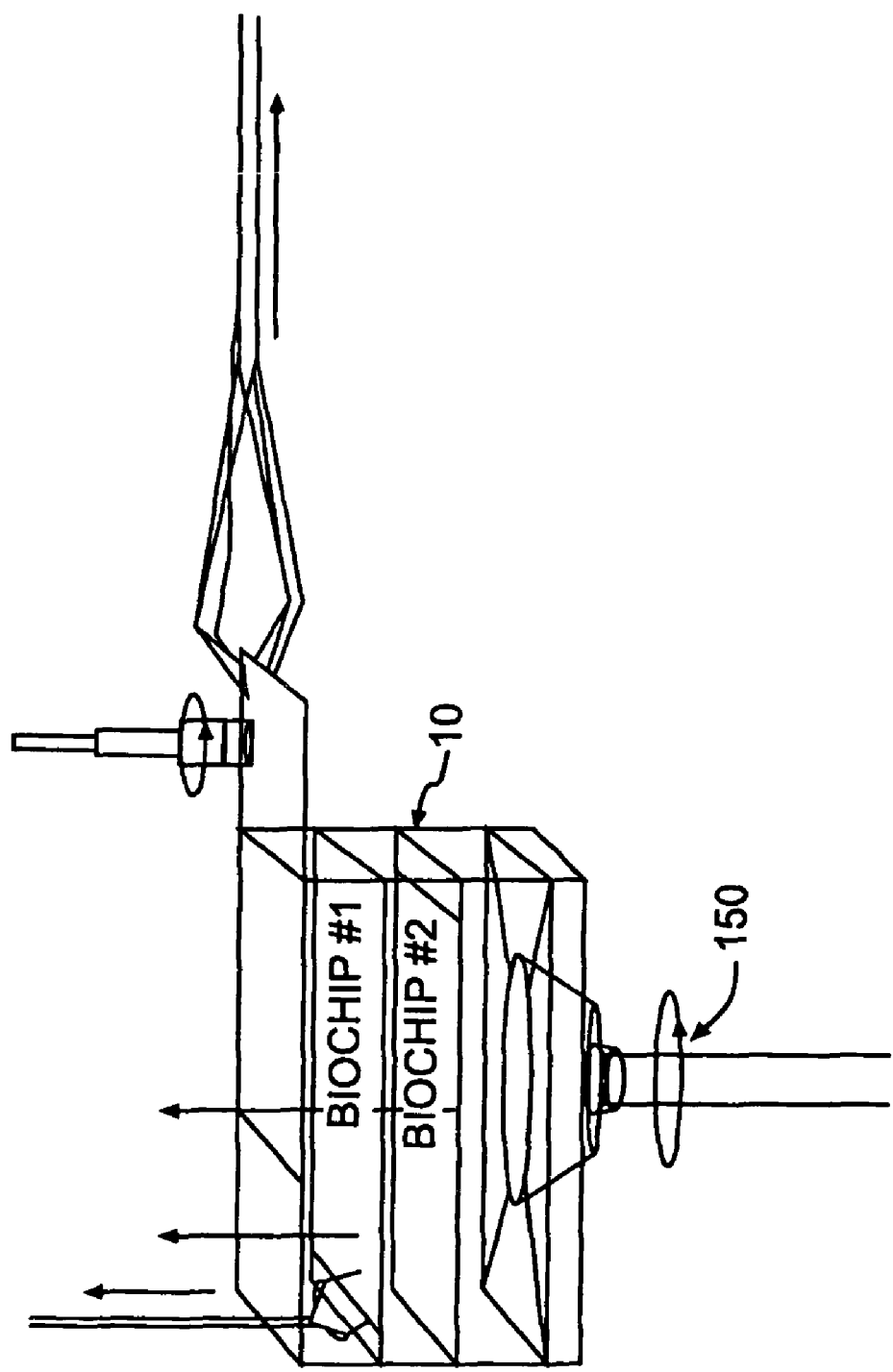
FIG. 6 illustrates removal of a screening capture device (10) from a blood collection apparatus.

As shown in FIG. 6, once blood collection is complete, the screening capture device (10) is removed from the blood collection apparatus, with its contents remaining sealed from the environment. For example, the inlet of the screening capture device (10) is unscrewed (or otherwise detached) from the collection needle or duct through which the blood of the donor is received. Likewise, the outlet of the screening capture device (10) is then unscrewed or unattached from the collection duct (150) through which the blood flow to the blood bag (200). The inlet and outlet of the screening capture device (10) may then be sealed so that it may be removed for further processing of the biochip. Sealing may be accomplished with a cap, plug, heat seal, weld or any other appropriate means. Of course, as discussed earlier, the invention also contemplates that a rapid assay mechanism may be provided in the screening capture device (10) itself so that the assay can be performed substantially simultaneously or soon after the blood collection is performed.

Preferably, the screening capture device (10) itself is then disassembled carefully by robotics in a controlled environment, with a lid (11) of the screening capture device (10) being removed first. Preferably, an O-ring is released when the right pressure is applied to a bracket/clip that keeps the lid shut, and the lid is preferably slid off horizontally. The biochips (20), (25) are then removed, preferably vertically, from their support brackets, which hold them in position in the screening capture device (10). The removed biochips (20), (25) are then inserted into a biochip processing system that supports the next stages of the screening process, such as amplification of captured or bound nucleic acid molecules, antigen/antibody reactions of captured binding partners, and detection of the target agents or molecules.

Figure 7A:
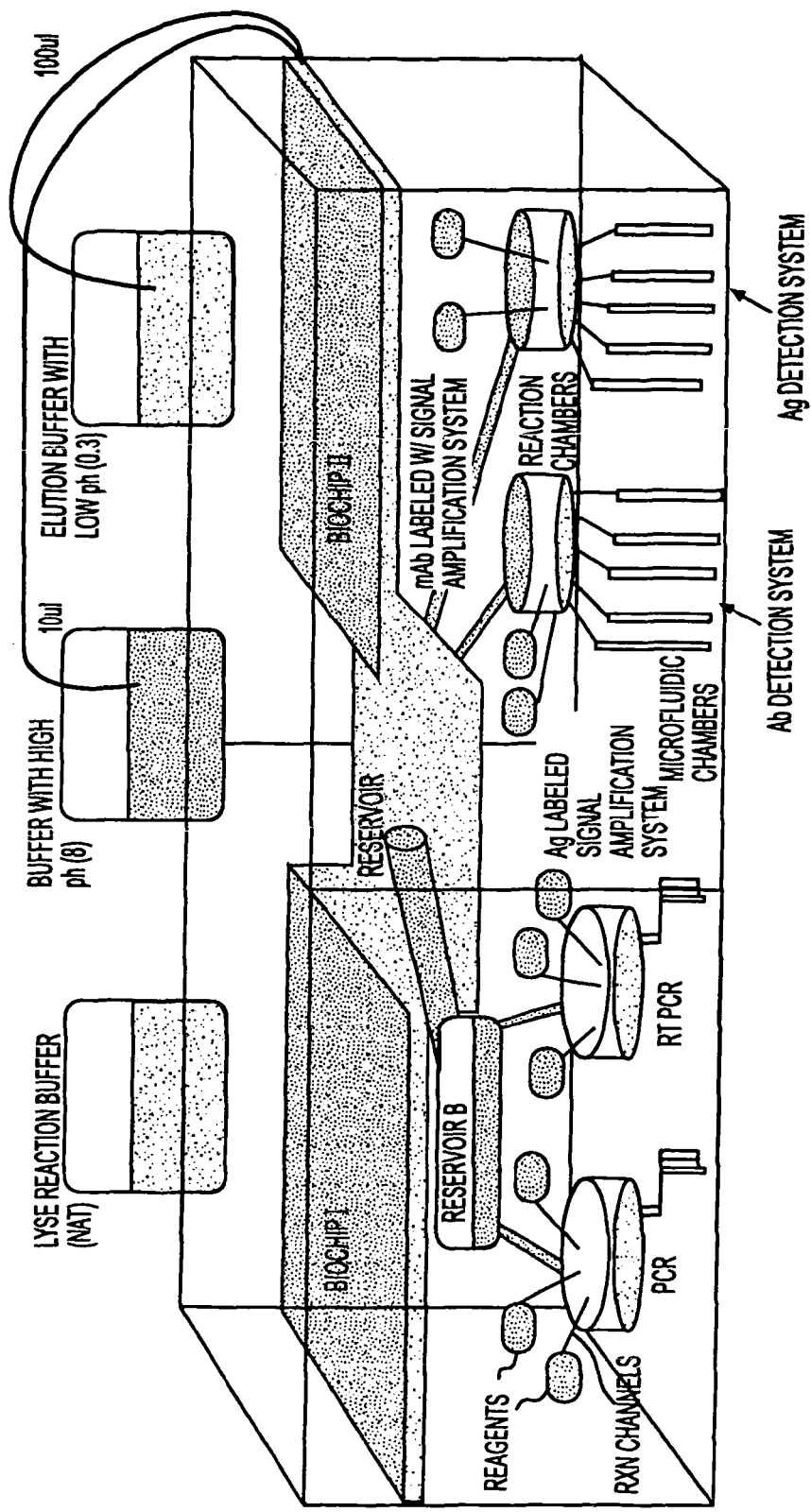
FIG. 7A illustrates a sealed bioprocessor that contains two separate sections sealed from one another—one for processing a NAT biochip and one for processing an immunoassay biochip.

The machine that the biochips are transferred to, the biochip processor, preferably is a self-sealed disposable unit. As shown in FIG. 7A, this sealed "laboratory on a chip" platform diminishes the chance for human error and prevents contamination of surrounding environments, as well as infection of lab workers. The biochip processor itself preferably contains two separate sections sealed from one another—one for processing a NAT biochip (I) and one for processing an immunoassay biochip (II), for running the NAT and immunoassays in parallel.

Figure 7B:
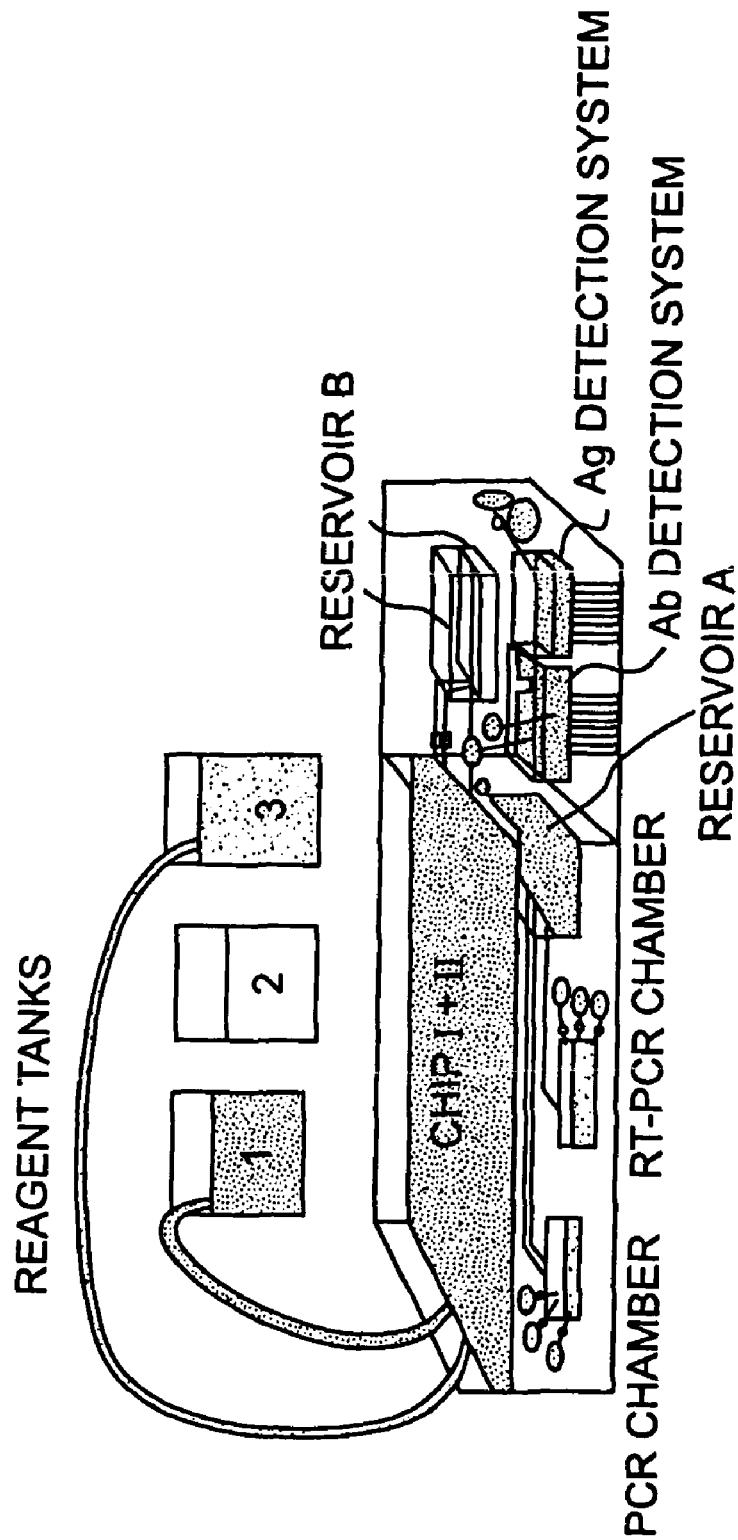
FIG. 7B illustrates an alternate embodiment of the bioprocessor in which there is only one biochip with two separate sections sealed from one another—one for processing the NAT biochip and one for processing the immunoassay biochip.

FIG. 7B provides an alternate embodiment of the biochip processor in which biochips I and II from FIG. 7A are combined into one biochip. In this embodiment the biochip is processed so as to release target molecules for the immunoassay under gentle elution conditions, followed by the harsher elution conditions to release nucleic acid target molecules from the virions and/or cells for the NAT assay.

Figure 8:
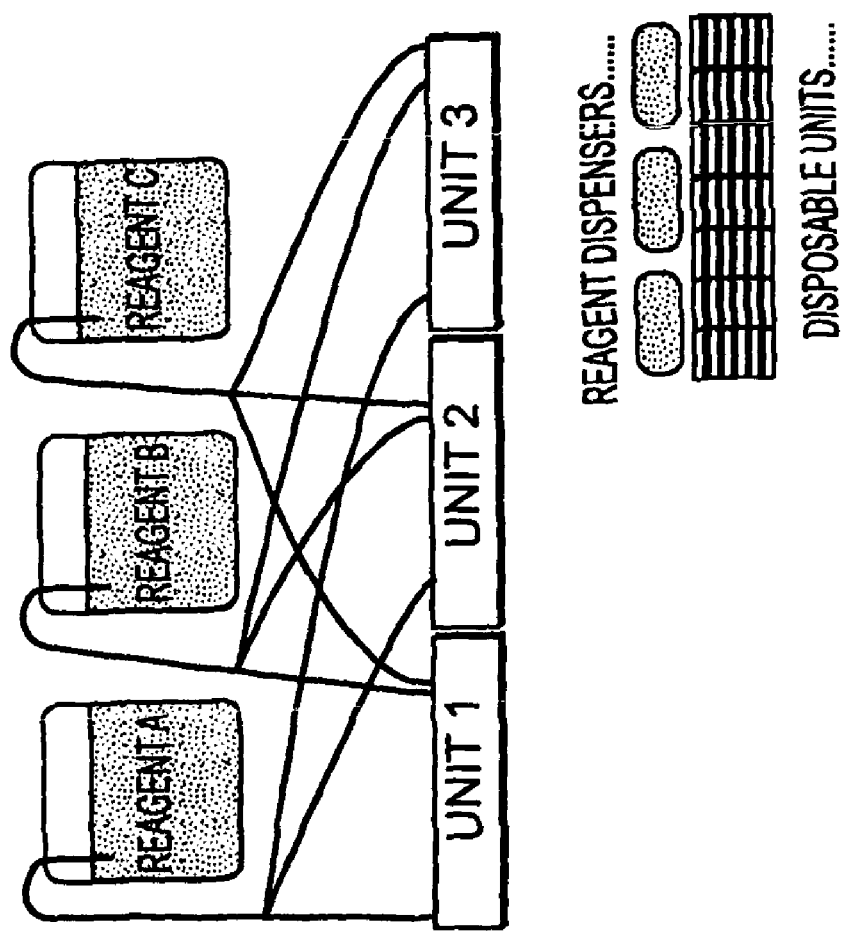
FIG. 8 illustrates the relationship of reagent containers to the bioprocessors.

In each of FIGS. 7A and 7B, the NAT portion of the biochip processor unit supports nucleic acid amplification reactions and a microfluidic detection system, and can be further adapted to other configurations to utilize other detection systems. The immunoassay portion of the unit supports antigen/antibody reactions with subsequent detection of target antigens or antibodies. The reagent(s) for each respective reaction are pumped into the two portions of the unit via connecting tubes as shown in FIG. 8. These tubes are disconnected from the unit once the assays are performed, and the unit is discarded. The reagents are stored in separate external bottles and can be kept through many uses. Biochip processors can be used as single testing units or can be run in parallel, allowing for many blood samples to be tested at once.

Amplification of nucleic acid sequences from Biochip I is a primary function of the NAT portion of the biochip processor unit. The self-contained machine in which the biochips are placed also contains an immunoassay portion for processing Biochip II, through interaction or binding of antibody and antigen. The biochips are locked, for example, into a position with a narrow space underneath the binding surface of about 0.25 mm, through which the elution and lysing buffers remain in contact with the biochip for a period of time and then pass through to a reservoir.

In the NAT system shown in FIGS. 7A and 7B, the immobilized target agents, molecules, cells or other components of interest are eluted from the biochip and, if necessary, lysed in appropriate elution and lysing buffers, resulting in target nucleic acid(s) in solution which collects in reservoir B prior to flowing to the PCR and/or RT-PCR chambers where amplification reactions occur. In one embodiment, PCR and RT-PCR are multiplexed, meaning that multiple primers and amplifiers are used to detect all eluted target nucleic acids or analytes. For example, from reservoir B, 50 µl is pumped into the PCR reaction chamber and another 50 µl is pumped into the RT-PCR reaction chamber. Standard PCR and RT-PCR reagents are present in the miniature wells located above the reaction chambers, allowing the force of gravity to pull reagents into the reaction chamber through reaction channels. Procedures utilized in the NAT portion of the biochip processor are based on standard PCR assays that are normally performed in a test tube. Standard PCR and RT-PCR protocols and reagents are known to persons skilled in the art, such as those disclosed in *Molecular Cloning, A Laboratory Manual*, $2^{nd}$ Ed., Sambrook et al., Chapter 14, Cold Spring Harbor Laboratory Press (1989), and in other scientific publications and manuals. The standard methods are easily adaptable for use in the NAT portion of the biochip processor. Particularly, the selection and amounts of the reagents and the assay conditions may be adapted from known PCR and RT-PCR methods.

In an alternate design, as shown in FIG. 7B, the biochips I and II are combined in one biochip processor. Instead of running the reagents for each biochip in parallel, they are run in sequence. Microprocessor controlled electronic valves may be used to control the flow of reagents and other solutions into the biochip processor so that the NAT assay and the immunoassay may be run sequentially.

Figure 9:
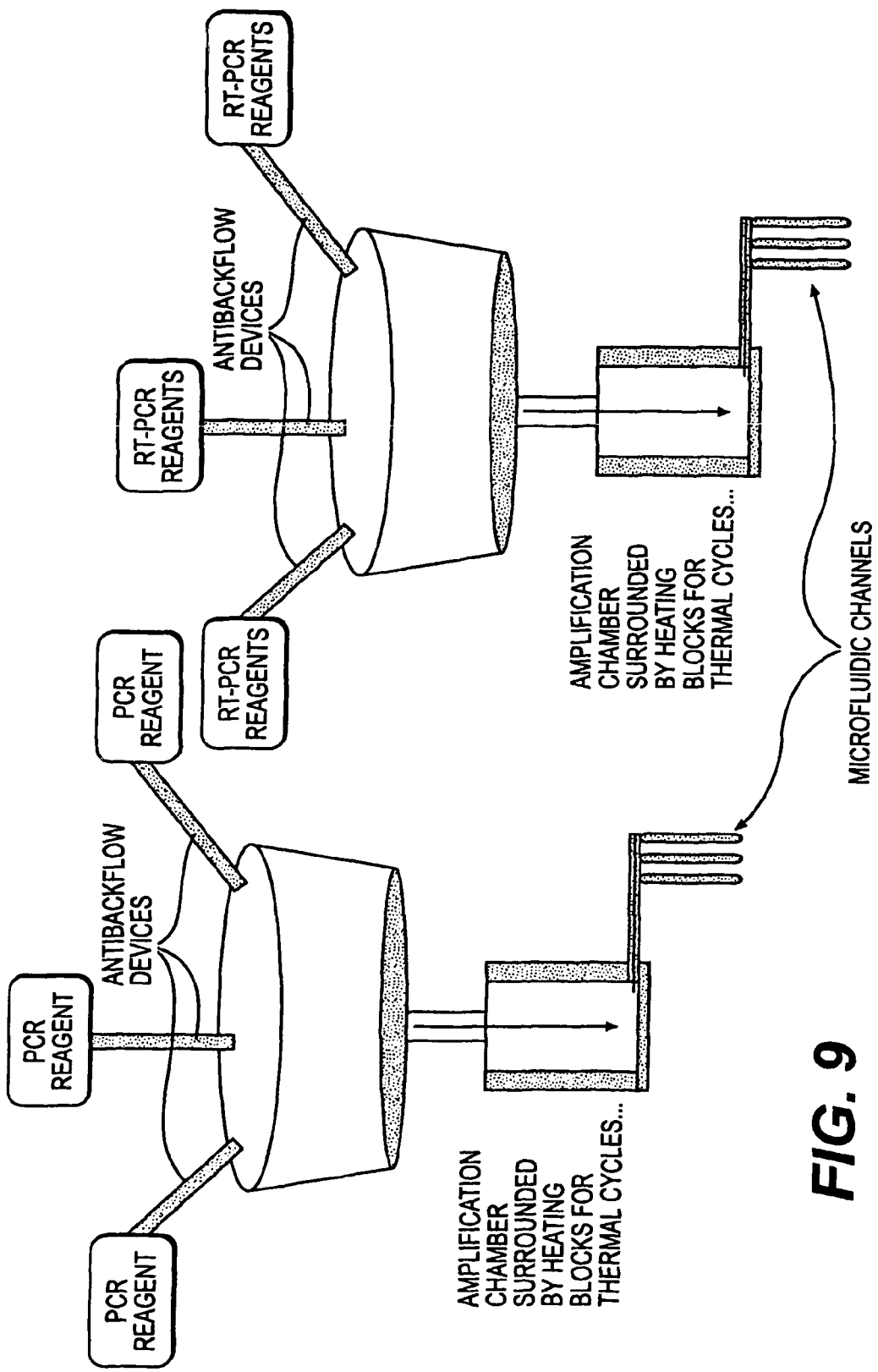
FIG. 9 illustrates a close-up view of PCR and RT-PCR reaction chambers and the relationship to the reaction channels, which contain devices to prevent backflow of reagents. Additionally, shown are the relationships of the reaction chambers to the amplification chambers to the microfluidity chamber.

As shown in FIG. 9, the reaction channels may have devices to prevent backflow of reagents. The limiting factor in this technology is enzyme reaction rate, and estimated amplification time is about 10 to 15 minutes. All reservoirs in the NAT system preferably are of the same volume, for example, about 200 µl, to avoid overflow. After reagents have mixed in the reservoirs, the mixture flows to separate amplification chambers surrounded by heating blocks for thermal cycling where for PCR and RT-PCR amplification occurs.

Figure 10:
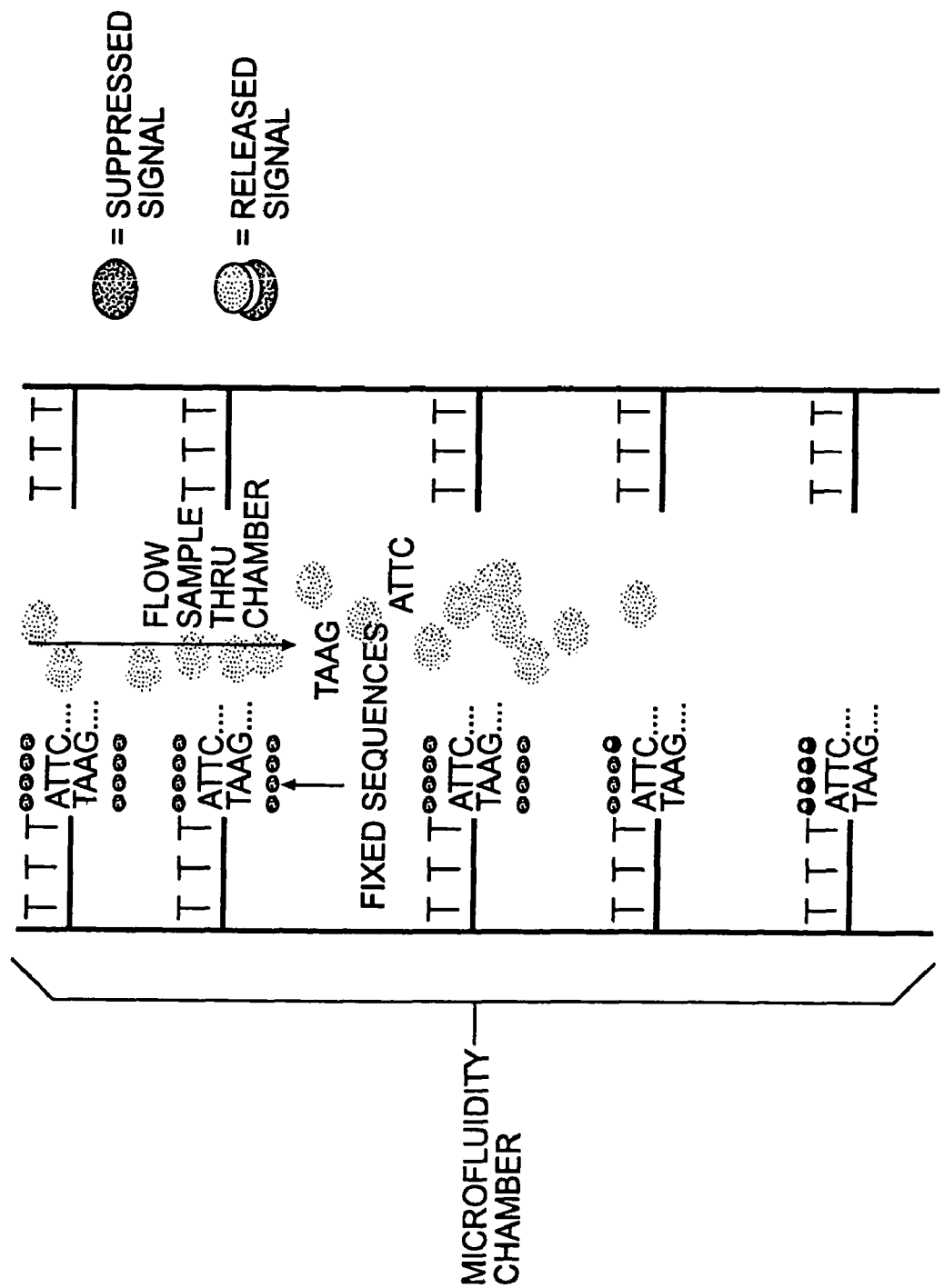
FIG. 10 illustrates a cross section of a microfluidic channel containing poly dT extenders with a detectable signal.

In certain embodiments shown in FIGS. 9 and 10, once the amplification process is complete in the NAT portion of the system, a small volume of sample, approximately 5 µl, enters a microfluidic device containing one or more microfluidic channels. The purpose of this microfluidic device is to detect whether a specific target nucleic acid is present in the blood utilizing the NAT screening system. The microfluidic channels contain capture molecules that are bound covalently to the interior walls of these channels. The channels can be made of any material that will allow covalent binding, such as plastic, rubber or other suitable materials. Such microfluidic channels are available from Caliper Technologies Corp., Mountain View, Calif. or from Fluidigm Corporation, South San Francisco, Calif. A sample flows through the chamber, whose walls contain poly dT extenders containing a detectable signal. The detection process involves hybridization of a target amplified nucleic acid sequence to matching sequences fixed within the microfluidity chamber and detection of this hybridization by chemiluminescence/fluorescent signaling.

Attached to the extenders are fluorescently marked sequences with quenched signaling. As the sample flows through the chamber, the amplified sequences hybridize with these fixed sequences, releasing the suppressed signal. The signal probes, each having a specific sequence designed to detect specific mutations, genotype and SNIPs, may be arrayed. Using such methods, the presence of a disease sequence can be detected, as well as point mutations based on the generation of signals. For an example of a nucleic acid sequence based amplification assay that utilizes quenched signaling, see Lanciotti and Kerst, J. Clinical Microbiology, pages 4506-13, (December 2001).

Also, by fixing variable chains in the chamber, different genotypes of each agent also are detectable. The principle behind heating the microfluidity chamber to an un-annealing temperature is to release the quenched fluorescent signal while allowing the NAT amplified sequences to complete hybridization to the sequences on the channel. If the sample sequences are complementary to the sequences on the channel, then that prevents the original sequences from annealing back and generating the quenched signal again. Detection may be visualized by digital CCD imaging of the signals given off within the chambers. Such cameras are available from Hamamatsu or other suppliers of detecting equipment. The signals can also be quantitatively measured by comparison with a standard or calibration signal.

The immunoassay portion of the biochip processing unit is employed to process Biochip #2, and uses an elution and neutralizing buffer solution to wash off the antibodies and antigens from Biochip #2. The antibody- or antigen-containing solution generated by elution is directed into two main reaction chambers—one for antibody detection (see FIGS. 11A, 11B and 11C) and one for antigen detection (see FIG. 12). The reaction chambers, which are about 200 µl in volume, are connected to reagent reservoirs positioned, for example, slightly above them via reaction ducts. The reagent for the antibody detection system contains antigens labeled with a signal amplification system, and the reagent for antigen detection contains monoclonal antibodies also labeled with a signal amplification system. The sample is exposed, in the reaction chamber, to about 2-5 µl of the reagents. Immunocomplexes of Ag-Ab-Samp (Ag=antigen, Ab=antibody (including polyclonal and/or monoclonal antibodies), Samp=signal amplification) form in the chambers if target Ag and Ab are present in the sample. After completion of the interaction and binding, the sample flows to separate microfluidic channels for detection.

The detection system used for antibody detection employs a capillary-like microfluidic channel heavily coated inside with monoclonal antibodies (mAbs), such as anti-human IgG mAb. These monoclonal antibodies recognize the Fc portion of the antibodies attached to the Ab-Ag-Samp. As for antigen detection, the microfluidic channels are heavily coated with monoclonal antibodies, such as goat anti-mouse IgG antibodies, that detect the antibody in the Ag-mAb-Samp immunocomplexes. For antigen detection, the signal amplification labeled monoclonal antibody is preferably from the rabbit species, such as that produced by Epitomics Corporation, South San Francisco, Calif. The complexes, along with other random non-target antibodies present in the sample, bind to the walls of the microfluidic channels. The channels are heavily coated, or coated in excess, with the desired monoclonal antibodies to avoid competition between non-target antibodies and target antibody complexes. Signal is only generated where immunocomplexes with target antibodies are bound. The entire channel can be viewed as a column with three major sections, as shown, for example, in FIGS. 11A and 12. The distribution of signals along the top, middle, and bottom sections of the channel provide an estimate of the concentration of target antibodies in the sample, which can be viewed by a CCD snapshot (digital camera). Such cameras are available from Hamamatsu or other suppliers of detecting equipment. As described above, the signal can be quantitatively measured by comparison to a standard or calibration signal.

Figure 11A:
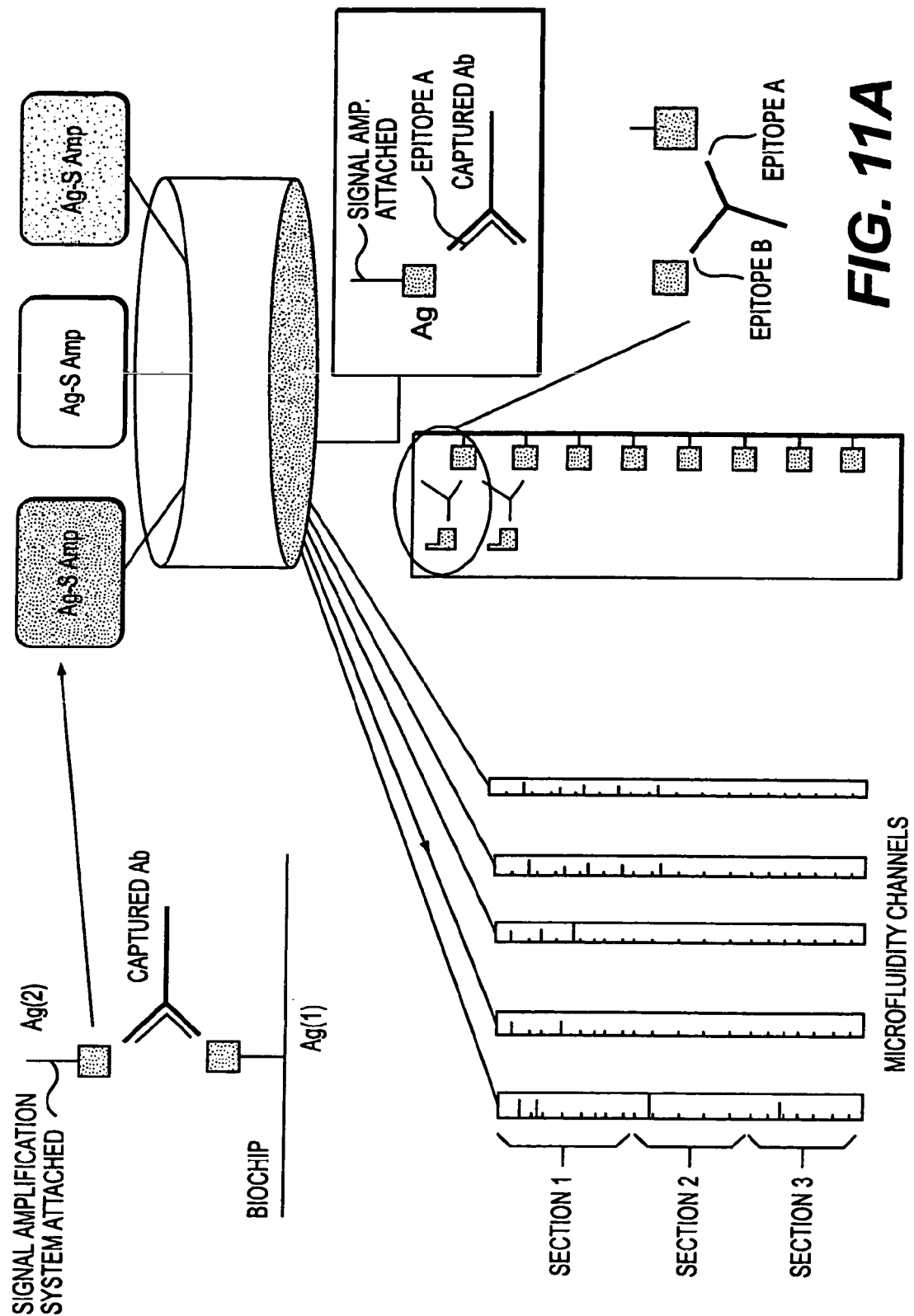
FIG. 11A illustrates a general overview of the immunoassay portion of the biochip processor as shown in FIGS. 7A and 7B for capturing and detecting antibody in the blood.

With reference to FIG. 11A, as a first example of an antibody assay, the microfluidity channels are coated with recombinant antigen A. The reaction chamber has recombinant antigen B with signal amplification molecules attached to form an immunocomplex with antibodies of the analyte. When the signal amplification molecules flow through the channel, the immunocomplex with specific signal amplification molecules attached will bind to the recombinant B antigen in the channel to generate a signal. This conjugated antigen-antibody from sample antigen in a solid phase sandwich assay configuration has proved to work for anti-HIV I/II assays.

Figure 11B:
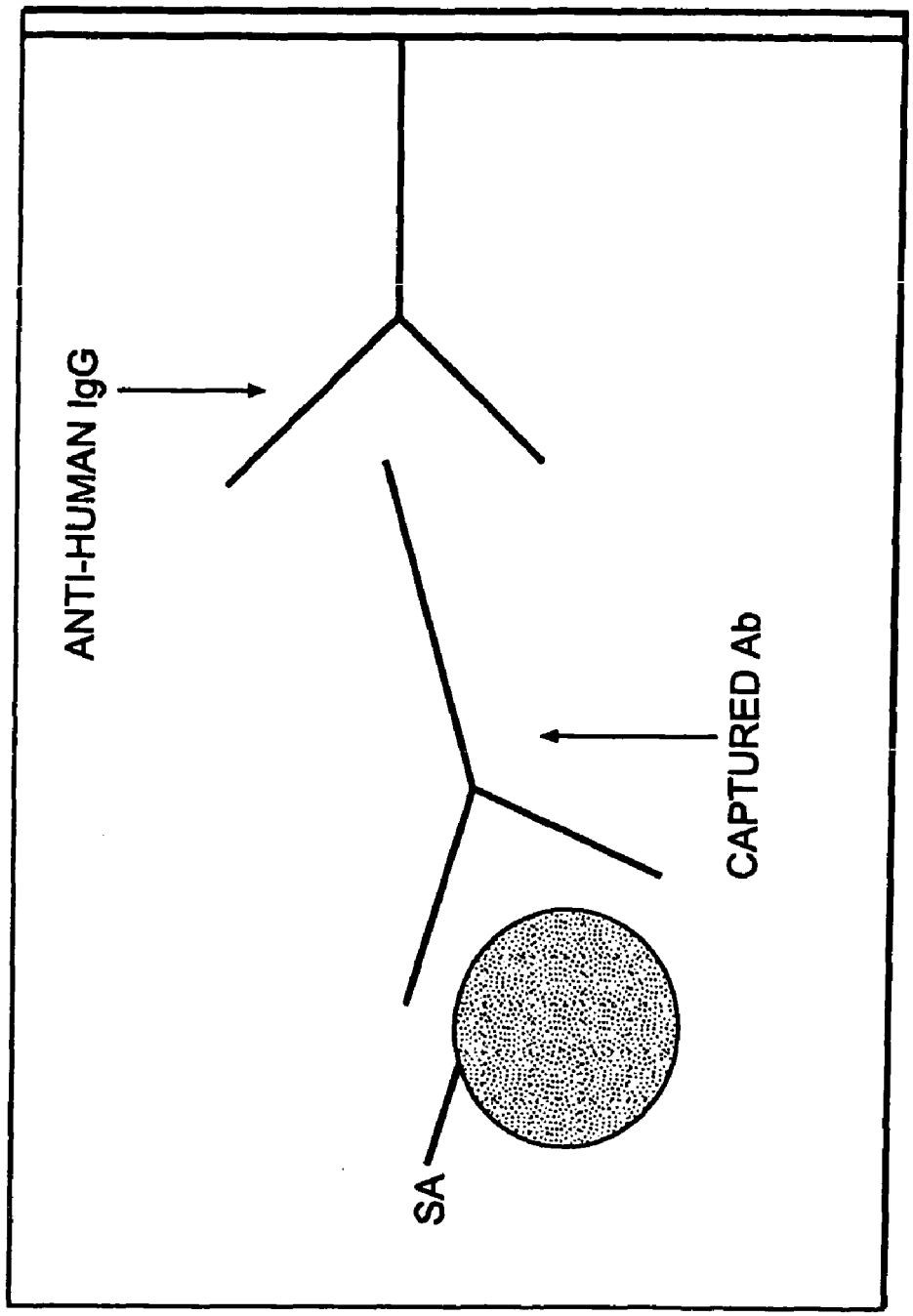
FIG. 11B illustrates an embodiment of an antibody detection method utilizing specially coated microfluidity channels containing anti-human IgG that are modified from the microfluidity channels of FIG. 11A.

As a second example of an antibody assay, as shown in FIG. 11B, the microfluidity channels may be coated with an anti-human IgG Fc antibody. The reaction chamber with labeled recombinant antigen to specific antibody to a signal amplification system will form immunocomplexes if the specific antibodies are present. When the immunocomplex with signal amplification molecules binds to the anti-human IgG Fc, it generates a signal. This assay works well when the anti-human IgG Fc on the channel exists in sufficient quantity.

Figure 11C:
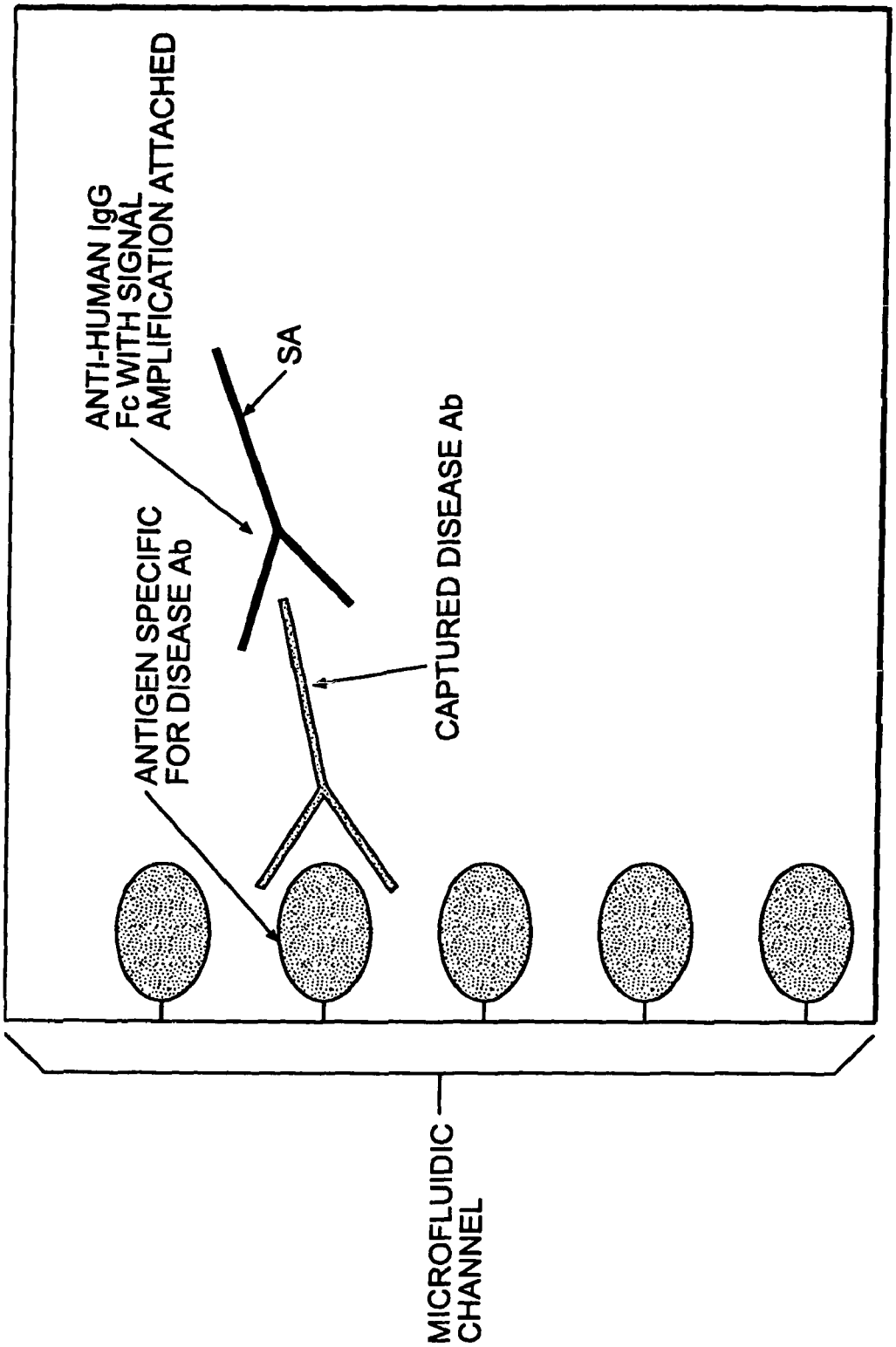
FIG. 11C illustrates an embodiment of an antibody detection method utilizing specially coated microfluidity channels containing antigen specific for an antibody directed against a disease to be detected that are modified from the microfluidity channels of FIG. 11A.

FIG. 11C depicts yet another example of an antibody assay that may be used with the present invention. Instead of exposing the eluted target (disease) antibodies to a labeled antigen reagent, they are exposed to an anti-human IgG Fc antibody labeled with a signal amplification system. The formed antibody-antibody immunocomplexes are then passed through a microfluidic channel coated with an antigen specific to the target antibody. In the presence of the target antibody, a complex illustrated in FIG. 11C (Ag>captured Ab>anti-human IgG Fc with signal amplification) will form and the detection will be completed with signal amplification.

Figure 12:
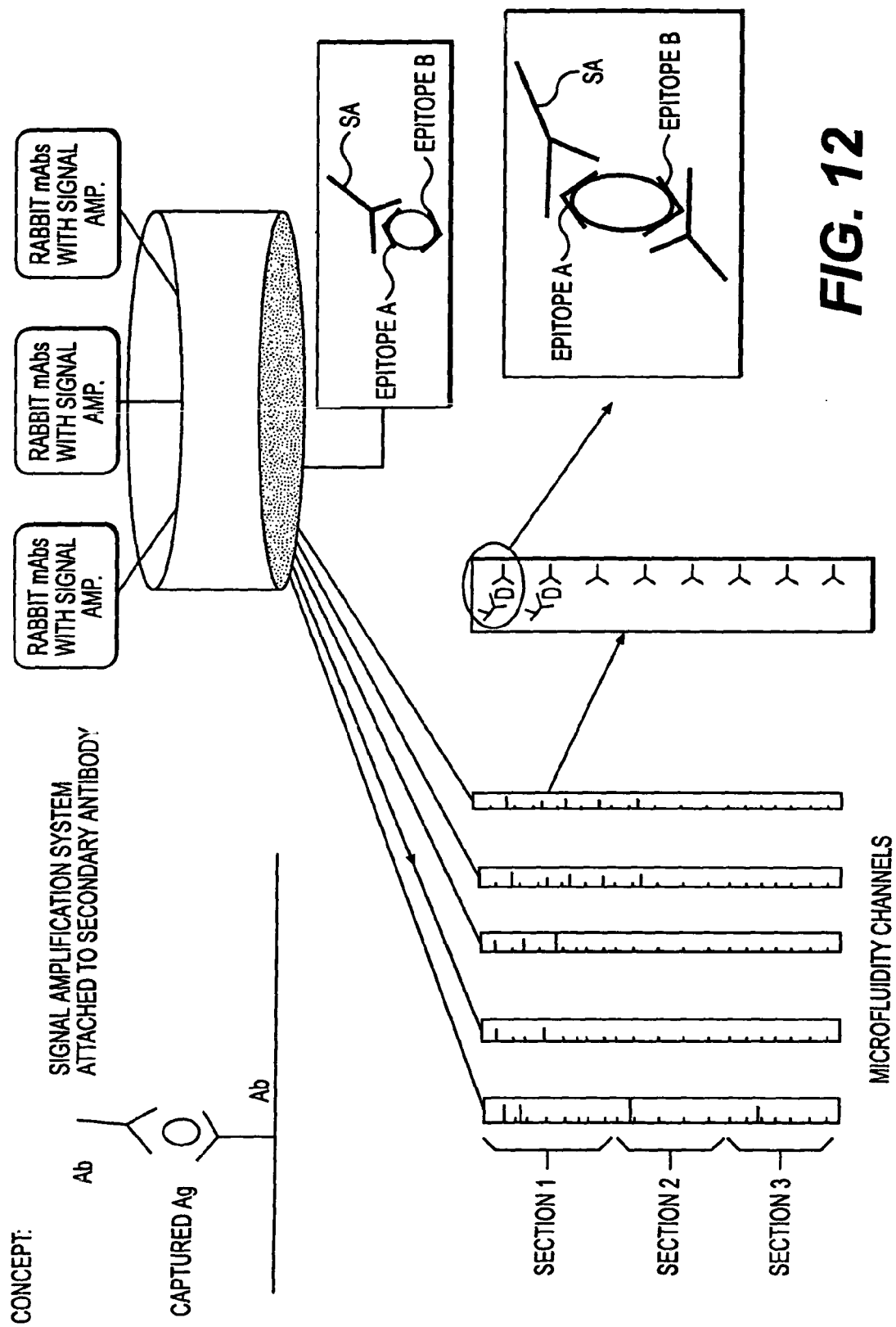
FIG. 12 illustrates a general overview of the immunoassay portion of the biochip processor as shown in FIGS. 7A and 7B for capturing and detecting antigen in the blood.

As one example for the antigen assay, shown in FIG. 12, the microfluidity channels are coated with a specific antibody to react to epitope "a" of analyte "A". In the meantime, within the reaction chamber has formed an immunocomplex of analyte A binding to another specific antibody that reacts to the epitope "b" on analyte A. The anti-epitope b antibody is conjugated to a signal amplification system. When the immunocomplex with the signal amplification molecules flows through the channel, the antibody that reacts to epitope "b" in the channel will bind with the epitope "a" on the immunocomplex to form a traditional sandwich immunoassay. The signal amplification system can be, for example, dextran sulfate or PEG molecules conjugated to nanocrystal molecules such as that provided by the Quantum Dot system.

Signal Amplification and Detection

As noted above, signal amplification may be necessary to detect target agents or molecules that are present at small quantities in blood. The inventive screening system, particularly the biochip processor, and screening methods are readily adaptable to such amplification.

In the case of nucleic acid targets, signal amplification can be accomplished by amplifying the target itself, using standard techniques, such as PCR. This is described above.

Alternatively, a signal itself may be amplified, which is particularly useful for detecting non-nucleic acid targets. For example, tyramide signal amplification (TSA) systems can enhance detection limits up to 100-fold with no loss in resolution, enabling users to see signals unobtainable by other methods. TSA, sometimes called CARD, for Catalyzed Reporter Deposition—is an enzyme-mediated detection method that utilizes the catalytic activity of horseradish peroxidase (HRP) to generate high-density labeling of a target protein or nucleic acid. TSA kits are commercially available.

Another example of a signal amplification system useful for detecting non-nucleic acid targets is described in Nam et al., Science, 301(5641): 1885-1886 (2003). This system employs a second antibody that recognizes a different epitope of targets than the capture antibody. The second antibody is conjugated to nanoparticles tagged with "bar code" DNA. The bar code DNA comprises numerous, perhaps thousands, of single-stranded DNA molecules having a known sequence. The bar code DNA can be amplified using standard PCR techniques and detected as any other nucleic acid target.

Reference to the following non-limiting examples will provide a fuller understanding of the claimed invention.

EXAMPLE 1

This example demonstrates the use of a biochip coated with antibody to capture corresponding antigen in blood and detection of the target antigen by mass spectroscopy.

Figure 13:
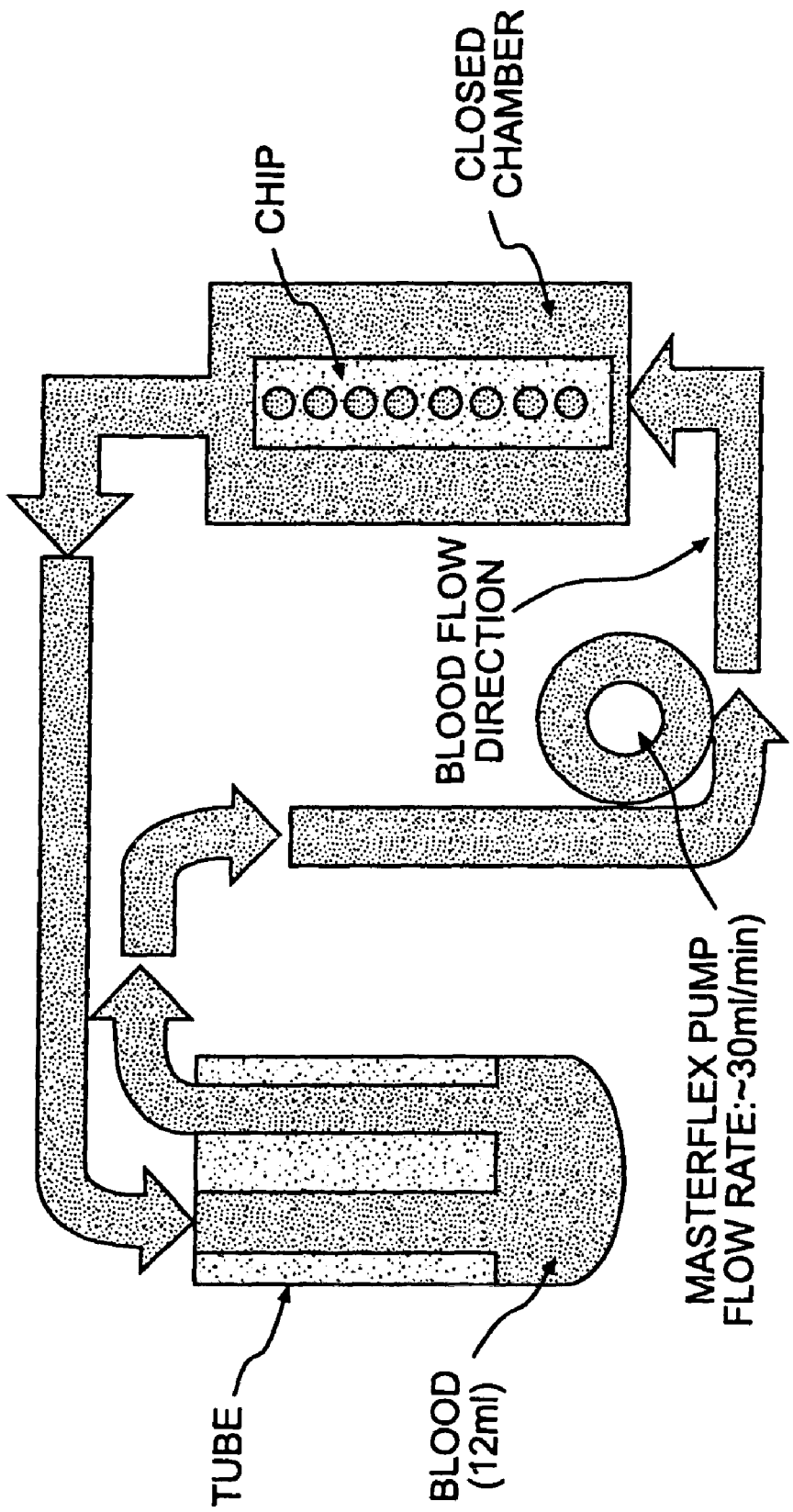
FIG. 13 illustrates an apparatus for simulating blood-drawing conditions, in which blood is pumped across a biochip.

A biochip (Ciphergen PS20 Protein chip) was covalently bound to a mouse monoclonal antibody against HIV P-24 core protein. The biochip then was placed in a tube where 12 ml of human blood was circulated a flow rate of about 30 ml/min at 37° C., to mimic the flow rate and temperature of a normal blood drawing. See FIG. 13. HIV P-24 antigen was spiked in the blood at a concentration of 0-200 ng/ml. After 10 min of circulation, the chip was removed and the bound antigen was detected by mass spectroscopy (Ciphergen Protein Chip Reader).

Figure 14:
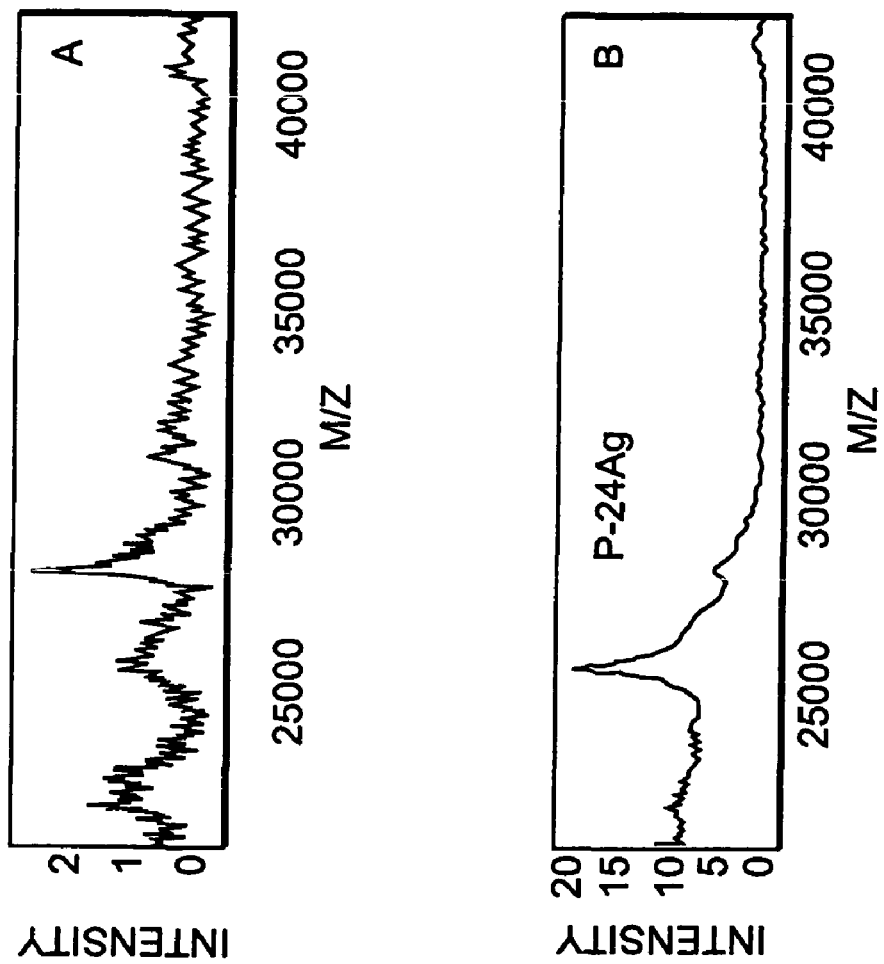
FIG. 14 shows that a biochip coated with monoclonal antibody against HIV P-24 antigen captured the antigen. In this example, the chip was coated by bovine IgG (A) or monoclonal antibody against HIV P-24 antigen (B). P-24 antigen was added to blood, and was captured by the chip that was coated by monoclonal antibody (B) as shown in the graph, but not by bovine IgG (A).

The results showed that antigen can be detected at a concentration of about 8 ng/ml in a 12 ml blood sample. FIG. 14 depicts a typical result.

EXAMPLE 2

This example demonstrates the use of a biochip coated with antigen to capture corresponding antibody in blood and detection of the target antibody by mass spectroscopy.

A biochip (Ciphergen PS20 Protein chip) was covalently bound to HIV P-24 core protein. The biochip then was placed in a tube where 12 ml of human blood was circulated at a flow rate of about 30 ml/min at 37° C., to mimic the flow rate and temperature of a normal blood drawing. Mouse monoclonal antibody against HIV P-24 was spiked in blood at a concentration of 0-20 ug/ml. After 10 min. of circulation, the chip was removed and the bound antibody was detected by mass spectroscopy (SELDI-MS from Ciphergen).

Figure 15:
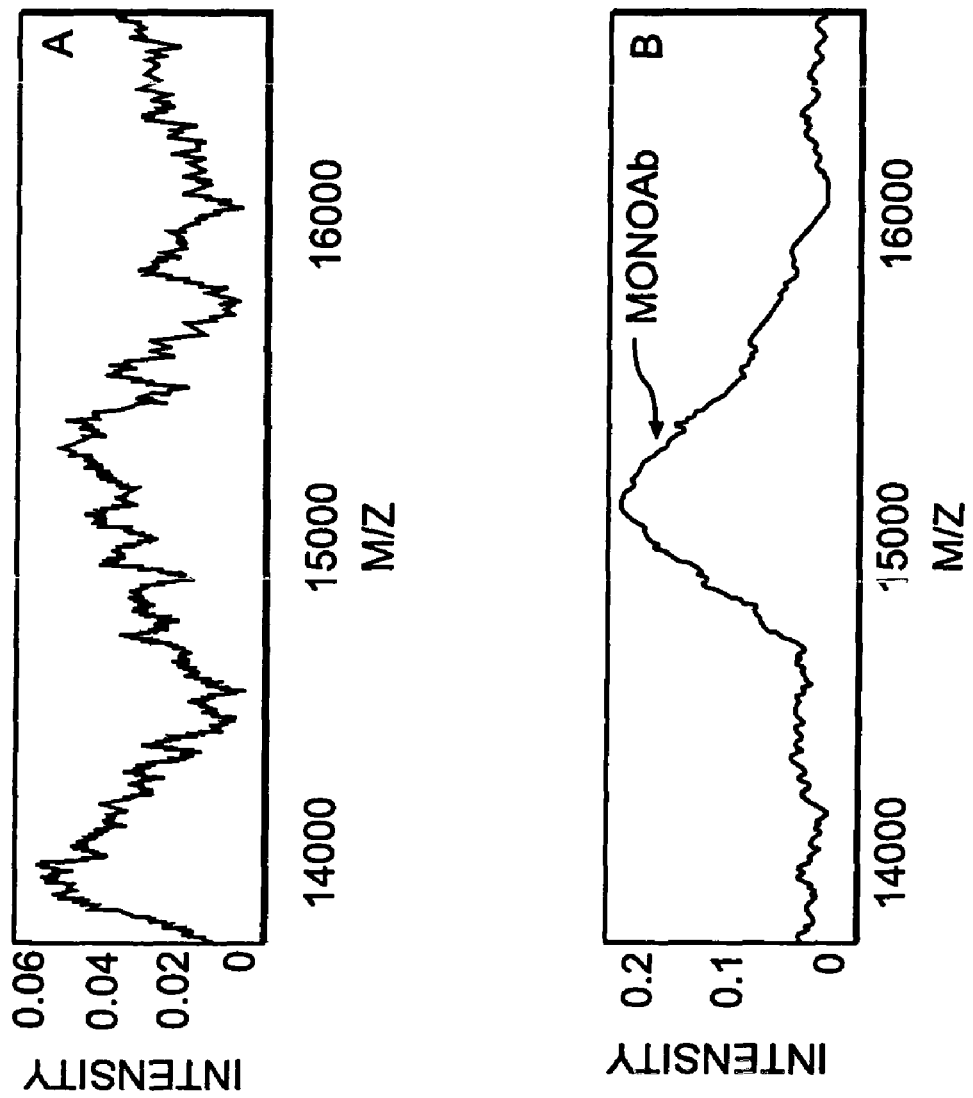
FIG. 15 shows that a biochip coated with HIV P-24 core protein captured anti-P-24 monoclonal antibodies. In this example, the chip was coated by HIV gp120 envelope protein (A) or HIV P-24 core protein (B). Monoclonal antibody (Mono Ab) against P-24 was added to blood, and was captured by the chip that was coated by P-24 antigen (B) as shown in the graph, but not by gp120 antigen (A).

The results showed that antibody can be detected at a concentration of about 1 ug/ml in a 12 ml blood sample. FIG. 15 depicts a typical result.

EXAMPLE 3

This example demonstrates the use of an antibody against viral surface protein to capture a virus in blood, followed by detection of viral nucleotides using a nucleic acid technology assay.

West Nile virus was captured by an Elisa assay. An Elisa plate was coated with West Nile Virus Monoclonal Antibody 3A3 (from BioReliance, Rockville, Md.) as a capture antibody. Purified West Nile virus samples then were added. After incubation, a polyclonal antibody (rabbit anti mouse West Nile virus, from BioReliance, Rockville, Md.) was added and incubated. The detection antibody was goat anti rabbit antibody conjugated with HRP. Other anti-West Nile virus antibodies, such as mouse monoclonal antibody 3.91D, also have been shown to capture West Nile virus. See, e.g., Hunt et al., 2002.

Table 1 (below) summarizes results of the virus-capture procedure.

TABLE 1

| Capture virus using monoclonal antibody. | | | |
|---|---|---|---|
| 1 Virus | 2 Viral Antigen PreM-3 | 3 Vero Cell Supernatant | 4 Sample diluent |
| 1.100 | | 0.295 | 0.208 |
| 0.554 | 0.118 | | 0.054 |

The absorbance (O.D.) was much higher in the samples containing virus or viral envelop antigen, columns 1 and 2, respectively. The negative control, vero cell supernatant, column 3, gave an O.D. reading very similar to the assay buffer background, column 4.

The experiment was repeated using human serum containing different concentrations of the virus culture. West Nile virus culture in 1:50 or 1:100 dilution was spiked to normal human serum and incubated at 37 C. for 10, 30 and 60 min. Table 2 summarizes results using human serum.

TABLE 2

| Capture virus in serum using monoclonal antibody. | | | |
|---|---|---|---|
| | Sample Incubation Time | | |
| | 1 Hr Signal | 30 min Signal | 10 min Signal |
| Normal human serum alone | 0.599 | 0.601 | 1.000 |
| 1:50 d | 1.608 | 1.361 | 1.119 |
| 1:100 d | 1.017 | 0.766 | 1.168 |

The signals were higher in the presence of the virus than its absence, and displayed a time-dependent manner. Similar results were obtained when the virus was spiked in whole blood (data not shown).

Following capture of the West Nile virus with antibody, the virus was lysed and viral RNA detected and quantitated by Taqman PCR. See, e.g., Shymala 2002, 2003(a) and 2003(b). Briefly, the captured viruses were suspended in 100 ul Taqman reagents and transferred to Taqman microtiter plate for detection by Taqman PCR. The Taqman reaction mix in a final volume of 100 ul contained, 50 ul One-Step RT PCR mix (Applied Biosystems, Inc., Foster City, Calif.), 1 pmol each of the amplification primers, and 0.4 pmol of the probe. The reaction conditions included 30 min at 48° C. for the RT reaction, 10 min at 95° C. to activate the Taq enzyme followed by 50 cycles of 30 secs at 95° C., alternating with 1 min at 60° C. in ABI 7900 Sequence Detector. Alternatively, the beads can be suspended in 100 ul of reaction mix containing 2 ul of Superscript III RT/Platinum Taq mix (Invitrogen Corporation, Carlsbad, Calif.), 50 ul of 2× Reaction mix, 4 mM $MgSO_4$, 2 ul of Rox, 1 pmol each of the amplification primers, 0.4 pmol of the probe. The reaction conditions include 15 min at 50° C. for the RT reaction, 2 min at 95° C. to activate the enzyme followed by 50 cycles of 30 sec at 95° C., alternating with 1 min at 60° C. in ABI 7900 Sequence Detector. PCR amplification primers corresponding to conserved regions within capsid (VWNV1-VWNV3) were chosen for robust amplification and detection. They were:

```
VWNVA1-CCGGGCTGTCAATATGCTAAA        (SEQ ID NO: 1)
(Sense Primer-nt129-149)

VWNVA2-AGCCCTCTTCAGTCCAATCAAG      (SEQ ID NO: 2)
(Anti-sense Primer-nt174-195)

VWNVA3-xCGGAATGCCCCGCGTGTTGz        (SEQ ID NO: 3)
(Probe-nt153-171).
```

Where X=6-FMA, and Z=linker plus Tamra.
(All numberings are as in GenBank deposit-AF196835)

An Internal control transcript of 750 nt, which is amplifiable by VWNAV1 and 2, but with an altered probe binding sequence and coupled to a different fluorophore, was used to detect PCR false negatives.

The publications and patent documents cited herein are incorporated in their entirety by reference, including the following:

Fortina, P. et al., *European J. Human Genetics* 8:884-894 (2000).

Fortina, P. et al., *Methods in Molecular Biology* 163:211-219 (2001).

Hunt, R. et al., *J. Clin. Microbiology* 40(6): 2023-2030 (2002).

Yuen, P-K. et al., *Genome Research* 11:405-412 (2001).

Petrick, J. *Vox Sanguinis* 80:1-11 (2001).

Gilles, P. N. et al., *Nature Biotechnology* 17:365-370 (1999).

Davies, H. et al., *Biotechnology* 27:1258-1261 (1999).

Carson, R. T. et al., *J. Immunol. Methods* 227:41-52 (1999).

Okamoto, T. et al., *Nature Biotechnology* 18:436-443 (2000).

Shyamala, V. et al., *Transfusion*. 43, p.128 (2003). Detection and Quantitation of West Nile Virus RNA by the Alternative NAT WNV Assay. 56th Annual AABB meeting, 56th Annual AABB meeting, 1st-4th November, San Diego, Calif.& XII APISBT 15th-18th November, New Delhi, India. ("Shyamala 2003(a)").

Shyamala, V. et al. (2003) Use of quantitative NAT assay to correlate West Nile Virus titration bioassasy (pfu/ml) with genomic copy numbers (geq/mL). 10th EPFA/

NIBSC workshop & SoGAT meeting, 3rd-4th July, Langen, Germany. ("Shyamala 2003(b)").

U.S. Prov. App. No. 60/480,431, filed Jun. 20, 2003: V. Shyamala, Identification of oligonucleotides for the capture, detection and quantitation of West Nile Virus.

Other embodiments of the invention will be apparent to those skilled in the art from a consideration of the specification and from the practice of the invention as disclosed herein; the invention embraces such other embodiments. Thus, this specification is exemplary only.

What is claimed is:

1. An in-line screening capture device for in-line screening of blood collected from a donor using a collection needle connected by a collection duct to a collection bag, comprising:
   an inlet for blood collected from the collection needle;
   a biochip unit that captures target agents or molecules from the blood; and
   an outlet that drains the blood from the in-line screening capture device to the collection duct,
   wherein chambers of the in-line screening capture device through which the blood flows have a cross-sectional area that is no smaller than that of the collection duct, and
   wherein the flow rate of the blood flowing through the in-line screening device is equal to the flow rate of blood collected in the absence of the device.

2. The in-line screening capture device according to claim 1, wherein the inlet of the in-line screening capture device is directly connected to a rear end of the collection needle.

3. The in-line screening capture device according to claim 1, wherein the inlet of the in-line screening capture device is connected directly to the collection needle.

4. The in-line screening capture device according to claim 3, wherein the inlet of the in-line screening capture device is connected directly to the collection needle so that the temperature of the blood in the in-line screening capture device is approximately 37° C.

5. The in-line screening capture device according to claim 1, wherein the biochip unit comprises a first biochip and a second biochip that are sequentially arranged between the inlet and the outlet.

6. The in-line screening capture device according to claim 5, wherein the first biochip and second biochip are arranged in a parallel stacked fashion.

7. The in-line screening capture device according to claim 5, wherein the first biochip is a nucleic acid amplification technique (NAT) biochip designed to run multiple tests on the first chip.

8. The in-line screening capture device according to claim 7, wherein the first biochip captures at least one infectious organism or cell containing a targeted nucleic acid molecule.

9. The in-line screening capture device according to claim 8, wherein the infectious organism is a virus, bacteria, fungi, protozoan, mycoplasma or prion and said cell is a cell from the donor of the blood sample.

10. The in-line screening capture device according to claim 5, wherein the second biochip is an immunoassay chip designed to run multiple assays on the second biochip.

11. The in-line screening capture device according to claim 10, wherein the second biochip captures targeted antigens or antibodies or a combination of targeted antigens and antibodies.

12. The in-line screening capture device according to claim 11, wherein the first and second biochips comprise covalently attached analytes.

13. The in-line screening capture device according to claim 5, wherein the first and second biochips are low density biochips.

14. The in-line screening capture device according to claim 5, wherein the in-line screening capture device comprises a lid that can be robotically removed to facilitate robotic removal of the first biochip and the second biochip.

15. The in-line screening capture device according to claim 1, wherein the dimensions of the in-line screening capture device are such that the flow rate of blood flowing through the in-line screening capture device is about 450 ml per 10 minutes.

16. The in-line screening capture device according to claim 1, wherein the dimensions of the inlet, the outlet, a surface area of biochips in the biochip unit, and the in-line screening capture device case are such that the collected blood maintains a constant flow rate through the in-line screening capture device.

17. The in-line screening capture device according to claim 1, wherein the target agent or molecule comprises at least one protein, nucleic acid molecule or fragment thereof indicative of or specific for a disease in a subject or an infectious agent.

18. The in-line screening capture device according to claim 17, wherein the protein is an antibody or an antigen.

19. The in-line screening capture device according to claim 1, wherein the outlet includes a funnel and a filter.

20. The in-line screening capture device according to claim 1, further comprising an anti-backflow device that prevents the blood from flowing back towards the inlet.

21. The in-line screening capture device according to claim 1, wherein the inlet and outlet are capable of being sealed when the screening capture device is removed from the collection needle and the collection duct.

22. An in-line screening capture device for in-line screening of blood collected from a donor using a collection needle connected by a collection duct to a collection bag, comprising:
an inlet for blood collected from the collection needle;
a biochip unit that captures target agents or molecules from the blood; and
an outlet that drains the blood from the in-line screening capture device to the collection duct,
wherein chambers of the in-line screening capture device through which the blood flows have a cross-sectional area that is no smaller than that of the collection duct,
wherein the flow rate of the blood flowing through the in-line screening device is roughly equal to the flow rate of blood collected in the absence of the device,
wherein the biochip unit comprises a first biochip and a second biochip that are sequentially arranged between the inlet and the outlet, and
wherein the first and second biochips comprise microarrays in which the analytes that bind to the target agent or molecule, if present in the blood, are arranged along the length of the biochips in the direction of blood flow over the first and second biochips, respectively.

23. An in-line screening system for in-line screening of blood collected from a donor using a collection needle connected by a collection duct to a collection bag, comprising:
an in-line screening capture device comprising:
an inlet for blood collected from the collection needle;
a biochip unit that captures target agents or molecules from the blood; and
an outlet that drains the blood from the in-line screening capture device to the collection duct,
wherein chambers of the in-line screening capture device through which the blood flows have a cross-sectional area that is no smaller than that of the collection duct;
wherein the flow rate of the blood flowing through the in-line screening device is roughly equal to the flow rate of blood collected in the absence of the device, and
at least one biochip processor for detecting at least one captured target agent or molecule.

24. The in-line screening system of claim 23, wherein said biochip processor is capable of amplifying said target agent or molecule.

25. The in-line screening system according to claim 23, wherein the biochip processor is a sealed disposable unit having a nucleic acid amplification technique (NAT) portion for processing a first biochip and an immunoassay portion for processing a second biochip.

26. The in-line screening system according to claim 25, wherein said target molecule is a nucleic acid molecule and the NAT portion comprises:
a biochip holder;
at least one reservoir for holding a sample;
at least one amplification reaction chamber connected to the reservoir; and
at least one detection component connected to the amplification reaction chamber.

27. The in-line screening system according to claim 26, wherein the NAT portion further comprises:
at least one reagent container connected to the reservoir; and
at least one reagent container connected to the reaction chamber.

28. The in-line screening system according to claim 27, wherein the NAT portion further comprises the first biochip held in the biochip holder.

29. The in-line screening system according to claim 28, wherein the first biochip is held such that a surface containing analytes is in contact with at least one elution and lysing buffer.

30. The in-line screening system according to claim 27, wherein the detection component is at least one microfluidity chamber.

31. The in-line screening system according to claim 25, wherein the target molecule is a target antibody or a target antigen and the immunoassay portion comprises:
a biochip holder;
at least one reservoir for holding a sample;
at least one reaction chamber connected to the reservoir; and
at least one detection component connected to the reaction chamber.

32. The in-line screening system according to claim 31, wherein the immunoassay portion further comprises:
at least one reagent container connected to the reservoir; and at least one reagent container connected to the reaction chamber.

33. The in-line screening system according to claim 32, wherein the immunoassay portion further comprises the second biochip held in the biochip holder, and wherein the second biochip is covalently attached to analytes that bind to the target antibody or the target antigen.

34. The in-line screening system according to claim 33, wherein the second biochip is held such that the attached analytes are in contact with at least one buffer.

35. The in-line screening system according to claim 31, wherein the detection component is at least one microfluidity chamber.

36. The in-line screening system according to claim 31, comprising at least two reaction chambers, one for the detection of a target antibody and one for the detection of a target antigen.

37. The in-line screening system according to claim 36, wherein each reaction chamber is connected to at least one detection component comprising at least one microfluidity chamber.

38. The in-line screening system according to claim 23, comprising more than one biochip processor.

39. A method of in-line screening of blood collected from a donor using a collection needle connected by a collection duct to a collection bag, comprising:
   providing a screening capture device comprising: an inlet for blood collected from the collection needle, a biochip unit that captures a target agent or molecule from the blood, and an outlet that drains the blood from the screening capture device to the collection duct;
   inserting the screening capture device between the collection needle and the collection duct proximate to the collection needle so that blood flowing through the screening capture device is approximately at a human body temperature; and
   allowing blood to flow through said screening capture device wherein the flow rate of the blood flowing through the screening capture device is equal to the flow rate of blood collected in the absence of the device.

40. The method of claim 39, further comprising the step of removing the screening capture device for further processing of the biochip unit.

41. The method according to claim 39, further comprising: robotically opening the screening capture device to remove the biochip unit; and
   inserting the biochip unit into a biochip processor for processing of biochips in the biochip unit.

42. The method according to claim 41, wherein the biochip processor comprises a nucleic acid amplification technique (NAT) portion for processing a first biochip and an immunoassay portion for processing a second biochip.

43. The method according to claim 42, wherein said target molecule is a nucleic acid molecule and the NAT portion comprises:
   a biochip holder comprising a first biochip;
   at least one reservoir for holding a sample eluted from the first biochip;
   at least one amplification reaction chamber connected to the reservoir; and
   at least one detection component connected to the amplification reaction chamber.

44. The method according to claim 43, wherein the NAT portion further comprises: at least one reagent container connected to the reservoir, wherein said method further comprises contacting the first biochip with at least one buffer from the reagent container that elutes and lyses the captured target agent or molecule from the first biochip to form a solution that collects in the reservoir.

45. The method according to claim 44, further comprising:
   pumping the solution in the reservoir to the at least one amplification reaction chamber;
   providing at least one additional reagent container that contains nucleic acid amplification reagents and allowing the reagents to flow into the amplification reaction chamber containing the solution;
   providing sufficient conditions to amplify at least one nucleic acid molecule in the solution; and
   detecting the presence of the amplified nucleic acid molecule in the detection component.

46. The method according to claim 45, wherein the detection component is at least one microfluidity chamber and detecting the presence of the amplified nucleic acid molecule by a nucleic acid hybridization method and the detection of a signal.

47. The method according to claim 42, wherein said target molecule is an antibody or an antigen and the immunoassay portion comprises:
   a biochip holder comprising a second biochip;
   at least one reservoir for holding a sample eluted from the first biochip;
   at least one reaction chamber connected to the reservoir; and
   at least one detection component connected to the reaction chamber.

48. The method according to claim 47, wherein the immunoassay portion further comprises: at least one reagent container connected to the reservoir, wherein said method further comprises contacting the second biochip with at least one buffer from the reagent container that elutes the captured target molecule from the second biochip to form a solution that collects in the reservoir.

49. The method according to claim 48, further comprising:
   pumping the solution in the reservoir into the at least one reaction chamber;
   providing at least one additional reagent container that contains a reagent comprising an antigen linked to a signal amplification system or an antibody linked to a signal amplification system and allowing the reagent to flow into the reaction chamber containing the solution;
   providing sufficient conditions to allow binding of the reagent to a target antibody or antigen in the solution; and
   detecting the presence of the target antibody or antigen in the detection component.

50. The method according to claim 49, wherein the detection component is at least one microfluidity chamber and detecting the presence of the signal by binding to an antibody immobilized on the wall of the chamber.

51. The method according to claim 47, further comprising utilizing more than one biochip processors in parallel.

52. The method according to claim 47, comprising at least two reactions chambers, one for the detection of a target antibody and one for the detection of a target antigen.

53. The method according to claim 52, wherein each reaction chamber is connected to at least one detection component comprising is at least one microfluidity chamber.

54. The method according to claim 41, further comprising utilizing more than one biochip processors in parallel.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgggctgtc aatatgctaa a                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agccctcttc agtccaatca ag                                             22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cggaatgccc cgcgtgttg                                                 19
```